United States Patent
Young et al.

(10) Patent No.: US 12,128,217 B2
(45) Date of Patent: *Oct. 29, 2024

(54) AUTOMATIC DRUG DELIVERY DEVICES

(71) Applicant: OVAL MEDICAL TECHNOLOGIES LIMITED, Cambridge (GB)

(72) Inventors: Matthew Young, Cambridge (GB); Ralph Lamble, Cambridge (GB)

(73) Assignee: OVAL MEDICAL TECHNOLOGIES LIMITED, Cambridge (GB)

( * ) Notice: Subject to any disclaimer, the term of this patent is extended or adjusted under 35 U.S.C. 154(b) by 228 days.

This patent is subject to a terminal disclaimer.

(21) Appl. No.: 17/658,969

(22) Filed: Apr. 12, 2022

(65) Prior Publication Data

US 2022/0233776 A1     Jul. 28, 2022

Related U.S. Application Data

(63) Continuation of application No. 16/258,036, filed on Jan. 25, 2019, now Pat. No. 11,324,890, which is a
(Continued)

(30) Foreign Application Priority Data

Oct. 17, 2012 (GB) .................................. 1218667
Feb. 28, 2013 (GB) .................................. 1303577

(51) Int. Cl.
*A61M 5/20*     (2006.01)
*A61M 5/00*     (2006.01)
(Continued)

(52) U.S. Cl.
CPC ........ *A61M 5/2033* (2013.01); *A61M 5/2066* (2013.01); *A61M 5/3287* (2013.01);
(Continued)

(58) Field of Classification Search
CPC .............. A61M 5/2033; A61M 5/2066; A61M 5/3287; A61M 5/19; A61M 2005/206; A61M 2005/2073; A61M 2005/208
See application file for complete search history.

(56) References Cited

U.S. PATENT DOCUMENTS 2,693,186 A    11/1954   Riker et al.
3,136,313 A    6/1964   Hands
(Continued)

FOREIGN PATENT DOCUMENTS

AU     2006217781 A1    8/2006
CN     87105155 A    1/1988
(Continued)

OTHER PUBLICATIONS

Office Action from corresponding European Application No. 20184753.0 dated Jun. 16, 2023.
(Continued)

*Primary Examiner* — Bradley J Osinski
(74) *Attorney, Agent, or Firm* — Lando & Anastasi, LLP

(57) ABSTRACT

The invention provides in one aspect a drug delivery device comprising a drug container assembly containing a drug, and a plunger positioned within the container assembly, the drug container assembly having an outlet for dispensing the drug, wherein, in an initial position, the outlet is sealed; a drive mechanism comprising a first stored energy source operable to apply pressure on the plunger or the drug container to pressurise the drug, and a first release mechanism operable to unseal the outlet after the drug has been pressurised. In another aspect, there is provided a drug delivery device comprising a housing, including an external housing portion configured to be held in use and a drug containing portion containing a drug, a needle assembly comprising a needle fixed to a needle hub, the needle hub configured to move relative to the drug containing portion
(Continued)

from an initial position within the housing to an insertion position in which the needle extends beyond the housing, a first stored energy source configured to move the needle hub from the initial position to the insertion position, and a plunger within the housing and configured to move relative to the drug containing portion to eject the drug through the needle when the needle is in the insertion position.

20 Claims, 35 Drawing Sheets

Related U.S. Application Data continuation of application No. 14/436,305, filed as application No. PCT/EP2013/071805 on Oct. 17, 2013, now Pat. No. 10,238,804.

(51) Int. Cl.
    *A61M 5/19*     (2006.01)
    *A61M 5/24*     (2006.01)
    *A61M 5/32*     (2006.01)

(52) U.S. Cl.
    CPC .............. *A61M 5/002* (2013.01); *A61M 5/19* (2013.01); *A61M 2005/2013* (2013.01); *A61M 2005/202* (2013.01); *A61M 2005/206* (2013.01); *A61M 2005/2073* (2013.01); *A61M 2005/208* (2013.01); *A61M 2005/2462* (2013.01); *A61M 2005/2474* (2013.01); *A61M 2005/2488* (2013.01)

(56) References Cited

U.S. PATENT DOCUMENTS

| | | | |
|---|---|---|---|
| 4,178,928 A | | 12/1979 | Tischlinger |
| 4,227,528 A | | 10/1980 | Wardlaw |
| 4,378,015 A | | 3/1983 | Wardlaw |
| 4,738,660 A | * | 4/1988 | Lucas ................. A61M 5/19 |
| | | | 604/157 |
| 5,085,641 A | | 2/1992 | Sarnoff et al. |
| 5,391,151 A | | 2/1995 | Wilmot |
| 5,620,421 A | | 4/1997 | Schmitz |
| 5,658,259 A | | 8/1997 | Pearson et al. |
| 5,709,662 A | | 1/1998 | Olive et al. |
| 10,238,804 B2 | | 3/2019 | Young et al. |
| 2003/0036725 A1 | | 2/2003 | Lavi et al. |
| 2006/0148634 A1 | | 7/2006 | Guter et al. |
| 2007/0073232 A1 | | 3/2007 | Pickhard |
| 2008/0039795 A1 | | 2/2008 | Slate et al. |
| 2008/0058732 A1 | | 3/2008 | Harris |
| 2008/0103490 A1 | * | 5/2008 | Edwards ............... G16H 20/17 |
| | | | 604/890.1 |
| 2008/0167624 A1 | | 7/2008 | Weston et al. |
| 2010/0036319 A1 | | 2/2010 | Drake et al. |
| 2010/0137832 A1 | | 6/2010 | Mathews et al. |
| 2010/0185178 A1 | | 7/2010 | Sharp et al. |
| 2011/0022001 A1 | | 1/2011 | Wei |
| 2011/0098656 A1 | | 4/2011 | Burnell et al. |
| 2011/0125100 A1 | | 5/2011 | Schwirtz et al. |

FOREIGN PATENT DOCUMENTS

| | | |
|---|---|---|
| CN | 1607968 A | 4/2005 |
| CN | 1874810 A | 12/2006 |
| CN | 101945680 A | 1/2011 |
| CN | 102112168 A | 6/2011 |
| CN | 102548599 A | 7/2012 |
| CN | 102573966 A | 7/2012 |
| CN | 103269730 A | 8/2013 |
| EP | 0409365 A1 | 1/1991 |
| EP | 0956061 A1 | 11/1999 |
| EP | 2364739 A1 | 9/2011 |
| EP | 2468336 A1 | 6/2012 |
| FR | 1514210 A | 2/1968 |
| GB | 2447787 A | 9/2008 |
| JP | H03118072 A | 5/1991 |
| JP | H03222962 A | 10/1991 |
| JP | 2004508897 A | 3/2004 |
| JP | 2006516436 A | 7/2006 |
| JP | 2007503853 A | 3/2007 |
| JP | 2007518507 A | 7/2007 |
| JP | 2009509605 A | 3/2009 |
| JP | 2011524212 A | 9/2011 |
| JP | 2012500696 A | 1/2012 |
| JP | 2012081283 A | 4/2012 |
| JP | 2012517845 A | 8/2012 |
| WO | 8505275 A1 | 12/1985 |
| WO | 9640360 A1 | 12/1996 |
| WO | 0147586 A1 | 7/2001 |
| WO | 0224259 A2 | 3/2002 |
| WO | 2007129324 A2 | 11/2007 |
| WO | 2011117592 A1 | 9/2011 |
| WO | 2011126439 A1 | 10/2011 |

OTHER PUBLICATIONS

Office Action from corresponding Japanese Application No. 2021-131725 dated Jul. 5, 2022.

Decision of Patent Grant of the Japanese Patent Office from corresponding JP Application Serial No. 2015-537271 dated Oct. 2, 2018.

Decision of Patent Grant of the Japanese Patent Office from corresponding JP Application Serial No. 2018-206423 dated Jan. 17, 2020.

English Translation of the First Office Action of the State Intellectual Property Office of the People's Republic of China from corresponding CN Application Serial No. 201380064999.X dated Nov. 30, 2016.

English Translation of the Notice of Reasons for Rejection from corresponding JP Application Serial No. 2015-537271 dated Sep. 5, 2017.

English Translation of the Second Office Action of the State Intellectual Property Office of the People's Republic of China from corresponding CN Application Serial No. 201380064999.X dated Sep. 27, 2017.

First Office Action of the State Intellectual Property Office of the People's Republic of China from corresponding CN Application Serial No. 201810511438.4 dated Aug. 3, 2020.

International Preliminary Report on Patentability from corresponding PCT Application No. PCT/EP2013/071805 dated Apr. 21, 2015.

International Search Report and Written Opinion from corresponding PCT Application No. PCT/EP2013/071805 dated Jun. 4, 2014.

Notice of Reasons for Rejection of the Japanese Patent Office from corresponding JP Application Serial No. 2020-032323 dated Feb. 9, 2021.

Office Action from corresponding Japanese Application No. 2018-206423 dated Oct. 8, 2019.

Office Action of the State Intellectual Property Office of the People's Republic of China from corresponding CN Application Serial No. 201810511438.4 dated Feb. 2, 2021.

Office Action from corresponding Indian Application No. 202118009282 dated Jun. 30, 2022.

* cited by examiner

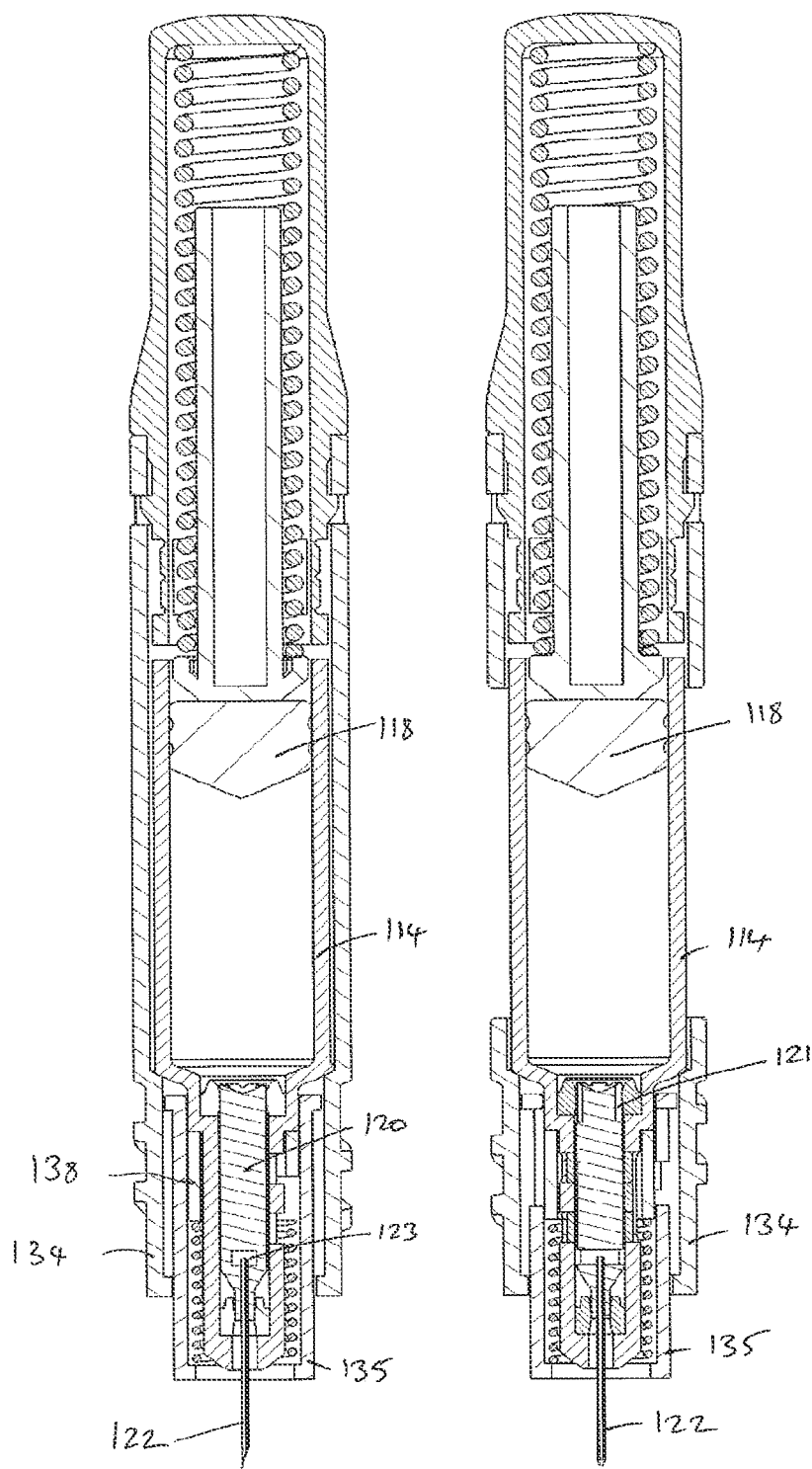

AUTOMATIC DRUG DELIVERY DEVICES

CROSS-REFERENCE TO RELATED APPLICATIONS

This application is a continuation of U.S. patent application Ser. No. 16/258,036, filed Jan. 25, 2019, which is a continuation of U.S. patent application Ser. No. 14/436,305, filed Apr. 16, 2015, which is a U.S. National Stage Application under 35 U.S.C. § 371 of International Application No. PCT/EP2013/071805, filed Oct. 17, 2013, which claims priority to Great Britain Patent Application No. GB 1218667.2, filed Oct. 17, 2012, and Great Britain Patent Application No. GB 1303577.9, filed Feb. 28, 2013. U.S. patent application Ser. No. 16/258,036, U.S. patent application Ser. No. 14/436,305 and International Application No. PCT/EP2013/071805 are each incorporated by reference herein in their entirety.

FIELD OF THE INVENTION

The present invention relates to automatic injectors, often referred to as autoinjectors that can provide both automatic needle insertion and automatic ejection of the drug through the needle.

BACKGROUND TO THE INVENTION

One type of drug delivery device known in the art is an autoinjector, which contains a medical, therapeutic, diagnostic, pharmaceutical or cosmetic compound (drug) before it is administered, and which is used to administer the compound through the skin of the patient via a hollow needle. Autoinjectors may be used by the patient themselves or by a different user, and are also used to administer drugs to animals.

Autoinjectors are typically used because they reduce the amount of training and effort needed by a user compared with that needed for a syringe, by automating either or both processes of inserting the needle into the patient and expelling the drug through the needle. They can also reduce the fear of injection by hiding the needle from the patient.

Some autoinjectors use a single spring to provide the motive power to both insert the needle into the patient and deliver the drug. Examples of this approach include the EpiPen autoinjector from Meridian and the Humira autoinjector from Abbot.

Autoinjectors typically include a pre-filled drug container to which a needle a fixed. In operation, the drug container is first driven forward to insert the needle into the patient and thereafter a plunger is driven through the drug container to eject the drug through the needle and into the patient. A single stored energy source, such as a spring may be used to provide the motive force for both needle insertion and drug injection, or separate stored energy sources may be provided.

Where an autoinjector includes only one spring to provide the force to drive both functions, the force that the spring provides for one of the functions may be higher than needed, to enable the spring to provide sufficient force for the other function. Advantageously the two functions happen one after another rather than simultaneously in order that the drug is delivered only after the needle is correctly positioned. Because the force provided by a spring typically reduces as the spring delivers energy, the spring inevitably provides a higher force for driving the first function, i.e. needle insertion, than for the following function i.e. drug delivery, whether or not this is desirable. The strength of the spring is determined by the requirement for the spring to be able to provide sufficient force and energy at every point during the drug delivery process. This often means that much higher force than is needed or desirable is provided during the needle insertion phase.

Where two springs are provided, complicated interlock mechanisms are required to ensure the correct sequence of operation and the number of layers of components required can become large and difficult to manufacture.

It is an object of the present invention to provide an autoinjector of reduced complexity, size, cost and operating noise.

SUMMARY OF THE INVENTION

The invention is defined in the appended independent claims, to which reference should be made. Preferred aspects of the invention are set out in the dependent claims.

In a first aspect, there is provided a drug delivery device comprising:
  a drug container assembly containing a drug, and a plunger positioned within the container assembly, the drug container assembly having an outlet for dispensing the drug, wherein, in an initial position, the outlet is sealed;
  a drive mechanism comprising a first stored energy source operable to apply pressure on the plunger or the drug container to pressurise the drug; and
  a first release mechanism operable to unseal the outlet after the drug has been pressurised.

The drug delivery device may be an autoinjector. The autoinjector may be configured to be manually held in operation or may be configured to be fastened to an injection site, for example with adhesive, to enable long delivery times. The drug may be a liquid.

The device may be configured such that the first release mechanism is operable only when a front end of the device, through which the drug is delivered, is pressed against an injection site. For autoinjectors, this is a good way to trigger drug delivery as it is simple, requires only one-handed operation and reduces the possibility of accidental operation. The device may further comprise a main housing, which may be part of or separate to the drug container assembly, and a skin contact element, the skin contact element forming a front end of the device (after uncapping), movement of the skin contact element relative to the main housing from an initial position to an insertion position operating or allowing the operation of the first release mechanism.

The device may comprise a second release mechanism operable to release the first stored energy source or store energy within the first stored energy source to pressurise the drug.

The device may be configured such that the first release mechanism cannot be operated until after the second release mechanism has been operated. For example, a second release mechanism may be triggered by removal of a cap or cover from the device and the first release mechanism may be triggered by pressing the uncovered front end of the device against an injection site. As used herein, front and proximal are used to mean the same end of the device, which is the end of the device through which drug is delivered to a patient.

Alternatively, the second release mechanism may be triggered by removal of the device from secondary packaging, by breaking a frangible element on the device or by operating a button or other trigger mechanism on the device.

The second release mechanism may move or release a bearing surface engaging the first stored energy source, to allow the first stored energy source to act on the plunger or drug container assembly to pressurise the drug. For example, the first stored energy source may be a compression spring and removal of a frangible strip from the device may allow a locking latch engaging the compression spring to move out of engagement with the compression spring so that the compression spring can partially expand so that it or an intermediate pusher component engages a rear surface of the plunger. In another example, removal of cap from a front end of the device may pull or allow the drug container assembly forward allowing a locking surface to move out of engagement with the compression spring so that the compression spring can partially expand so that it or an intermediate pusher component engages a rear surface of the plunger.

In other embodiments, the drive mechanism may form a first sub-assembly and the drug container and first release mechanism may form a second sub-assembly, wherein the device is configured such that energy is stored within the first stored energy source as the first sub-assembly is connected to the second sub-assembly. For example, the first stored energy source may be a compression spring. The compression spring may be compressed between the first sub-assembly and the second sub-assembly as the first sub-assembly is connected to the second sub-assembly. The first sub-assembly may be connected to the second sub-assembly by a screw fitting or a mechanical interlock fitting. The first stored energy source may pressurise the drug as the first sub-assembly is connected to the second sub-assembly. In the example above, the compression spring may be compressed between a rear surface of the plunger and a housing portion of the first sub-assembly as the first sub-assembly is connected to the second sub-assembly.

The first sub-assembly may be configured to be disconnected from the second sub-assembly so as to be re-usable with a different second sub-assembly. For example, the first sub-assembly and second sub-assembly may be configured to allow the first sub-assembly to be unscrewed from the second sub-assembly. The second sub-assembly may be a consumable item, containing a pre-measured dose of drug but the first subassembly may be reused with a plurality of different second sub-assemblies to deliver successive doses of the drug or different doses or doses of different drugs.

The device may comprise a hypodermic needle through which the drug is delivered in use.

An interior of the needle may be not in contact with the drug before operation of the first release mechanism.

The device may comprise a needle insertion mechanism configured to insert the needle into the injection site automatically. Alternatively, in use, needle insertion may be performed manually by the action of the user pressing the device against an injection site.

Operation of the first release mechanism may release the needle insertion mechanism and unseal the outlet. In this way, a single user action can be used to trigger both needle insertion and drug delivery. Of course, as an alternative, it is possible to configure the device so that a separate user action is required to trigger drug delivery following needle insertion, whether that is automatic or manual.

The needle insertion mechanism may operate to move the needle relative to the drug container assembly. The drug container assembly may be held within a main housing of the device and may remain fixed relative to the main housing during operation of the device. It is then not necessary to move the mass of the drug container assembly through the housing during a needle insertion operation. This reduces the size of the device and the noise during operation.

The device may be configured such that the hydraulic pressure of the drug, provided by the release of the first stored energy source, is used to move the needle insertion mechanism. Typically, the amount of force required for needle insertion is a fraction of the force required to push the drug through the needle. By selecting the area of the surface on which the drug acts to move the needle, an appropriate fraction of the force applied to the drug by the drive mechanism can be transferred to the needle insertion mechanism.

In one embodiment, the needle is provided in a needle hub that extends into the drug container assembly and, in an initial position, seals the outlet. The needle hub is restrained from proximal movement by a locking element, wherein the first release mechanism is operable to release the needle hub from the locking element so that it can be driven by the pressure of the drug in a proximal direction. The needle hub is configured such that movement of the needle hub in a proximal direction from the initial position to an insertion position unseals the outlet, allowing the drug to pass from the drug container through the needle to the injection site.

Alternatively, the needle insertion mechanism may comprise a second stored energy source, such as a compression spring, that is released by the first release mechanism.

In one embodiment, the needle is provided in a needle hub that, in an initial position, seals the outlet, wherein needle hub is restrained from proximal movement by a locking element, wherein the first release mechanism is operable to release the needle hub from the locking element so that it can be driven by the second stored energy source in a proximal direction and wherein the needle hub is configured such that movement of the needle hub in a proximal direction from the initial position to an insertion position unseals the outlet, allowing the drug to pass from the drug container through the needle to the injection site.

The needle insertion mechanism may be arranged such that the needle hub and plunger move along the same or along different axes. For example, the device may be configured such that, in use, the needle hub and plunger move parallel to one another. Alternatively, in use, the needle hub may move in a direction non-parallel, such as perpendicular, to the direction of movement of the plunger. The arrangement of needle and drug container assembly may be configured to provide the desired overall shape and size for the device.

The device may comprise two or more drug container assemblies each containing the same or different drugs, each having an associated drive assembly, wherein the device is configured such that the drug from each container is delivered through the same needle.

At least one drug container assembly may have a separation seal that seals the drug in that container from the drug in the other drug container or drug containers, or that separates two different drugs with in the same container. Operation of the associated drive mechanism may automatically unseal the separation seal. This arrangement allows the construction of a delivery device containing two or more different drug components that are only mixed just before or during delivery.

In another embodiment, the device may comprise a sealing member sealing the outlet, wherein the first release mechanism is configured to move a piercing member relative to the sealing member to pierce the sealing member and so unseal the outlet.

Alternatively, the first release mechanism may operate to open a valve that seals the outlet. For example, the first release mechanism may displace a needle hub component relative to the drug container assembly to unseal the outlet. The device may further comprise a first sealing member that seals a distal end of the needle and a second sealing member that provides a seal between an exterior of the needle and the drug container assembly, wherein the first release mechanism displaces the needle relative to the first sealing member to unseal the distal end of the needle.

The drug container assembly may comprise an expandable portion, such as a concertina shaped portion, to allow a front portion of the drug container assembly to move away from a rear portion of the drug container assembly while remaining fluid tight. The needle hub may be fixed to the front portion of the drug container assembly. A first sealing member may be fixed to the rear portion.

Alternatively, the first release mechanism may displace the needle relative to the second sealing member from an initial position to an insertion position, wherein the second sealing member provides a seal between an exterior of the needle and the drug container assembly as the needle moves from the initial position to the insertion position.

In one embodiment, the needle comprises a proximal end for insertion into a patient and a distal end for receiving the drug, and the needle hub further comprises a sealing portion configured to seal the outlet when the needle hub is in an initial position and wherein the needle hub comprises an inlet portion positioned around a distal end of the needle, the inlet portion providing fluid communication between the outlet and the distal end of the needle when the needle hub is in an insertion position.

The device may further comprise a second sealing element that provides a seal around the needle hub to the keep needle sterile in an initial position.

In the embodiments referred to, the needle hub has been generally described as moving in a proximal direction to unseal the outlet. It should be clear that it possible to configure the device such that distal movement of needle hub is effective to unseal the outlet.

The required seals may be formed using any suitable materials. For example, elastomeric o-ring seals and elastomeric plugs or rigid surfaces may be used with a mechanical interference fit.

The needle hub may rotate between the initial position and the insertion position. This may be in addition to, or in the absence of, translational movement of the needle hub. For example, the device may be configured for manual needle insertion such the needle does not move relative to the main housing during operation. However, movement of a skin contact element during needle insertion may drive a cam surface on the needle hub to rotate relative to the drug container assembly to open the outlet.

In the embodiments described, generally the plunger moves through the drug container and relative to an injection site to deliver the drug from the drug container. However, as an alternative, the plunger may be static relative to the injection site, with the drug container moving relative to the plunger to deliver the drug from the drug container.

The first release mechanism may comprise a first locking surface on the skin contact element that in the initial position limits relative movement between a needle hub and the main housing or drug container assembly. The device may further comprise a biasing element between the skin contact element and the housing or drug container assembly, the biasing element urging the skin contact element in a proximal direction. Following delivery of the drug and removal of the device from the injection site, the biasing element may urge the skin contact element proximally to a final position covering the needle.

Pressurising the drug and subsequently unsealing an outlet to delivery the drug typically leads to a quieter delivery mechanism, which is preferred by end users. It also allows for simpler front-end activation of the device and a needle insertion mechanism and outlet unsealing mechanism that need not be linked to the drive mechanism at the rear of the device. This allows for smaller, less expensive drug delivery devices to be made.

In a second aspect, there is provided a drug delivery device comprising:
  a housing, including an external housing portion configured to be held in use and a drug containing portion containing a drug;
  a needle assembly comprising a needle fixed to a needle hub, the needle hub configured to move relative to the drug containing portion from an initial position within the housing to an insertion position in which the needle extends beyond the housing;
  a first stored energy source configured to move the needle hub from the initial position to the insertion position; and
  a plunger within the housing and configured to move relative to the drug containing portion to eject the drug through the needle when the needle is in the insertion position.

The drug containing portion may be integral with or fixed relative to the external housing portion. The drug delivery device may an autoinjector.

The device may further comprise a second stored energy source configured to move the plunger through the drug containing portion. Movement of the needle hub from the initial position to the insertion position may trigger a release of the second stored energy source.

Alternatively, the first stored energy source may provide the motive force for both needle insertion and ejection of the drug through the needle. In that case, the needle hub may be moved from the initial position to the insertion position by the pressure of the drug acting on the needle hub.

The housing may comprise a skin contact element, the skin contact element being movable relative to the external housing portion to release the first stored energy source or to unlock a release for the first stored energy source.

The device may further comprise a sealing element fixed to the drug containing portion and positioned around a shaft of the needle, the sealing element maintaining a fluid tight seal around the shaft of the needle as the needle moves from the initial position to the insertion position.

The drug containing portion may have a first end and a second end, wherein the plunger moves from the first end to the second end to eject the drug, and wherein the needle hub extends between the first and second ends of the drug containing portion. The needle may be not in fluid communication with the drug in the initial position.

The needle hub and the plunger may move along different axes.

The needle may comprise a proximal end for insertion into a patient and a distal end for receiving the drug, and the device may further comprise a sealing element fixed to the needle and configured to seal the drug containing portion when the needle hub is in the initial position and the needle hub may comprise an inlet portion positioned around a distal end of the needle, the inlet portion providing fluid communication between the drug containing portion and the distal and of the needle when the needle hub is in the insertion position.

In a third aspect, there is provided a drug delivery device comprising:
- a housing;
- a drug container containing a drug;
- a needle assembly comprising a needle fixed to a needle hub, the needle hub configured to move relative to the drug containing portion along a first axis from an initial position within the housing to an insertion position in which the needle extends beyond the housing;
- a first stored energy source configured to move the needle hub from the initial position to the insertion position; and
- a plunger within the housing and configured to move along a second axis through the drug containing portion to eject the drug through the needle when the needle is in the insertion position;
- wherein the first and second axes are not coaxial.

In a fourth aspect, there is provided a drug delivery device comprising:
- a housing;
- a drug container containing a drug;
- a needle assembly comprising a needle fixed to a needle hub, the needle hub configured to move relative to the drug containing portion from an initial position within the housing to an insertion position in which the needle extends beyond the housing;
- a first stored energy source configured to move the needle hub from the initial position to the insertion position;
- a plunger within the housing and configured to move through the drug containing portion to eject the drug through the needle when the needle is in the insertion position; and
- a second stored energy source configured to move the plunger through the drug containing portion to eject the drug;
- wherein movement of the needle assembly from the initial position to the insertion position releases the second stored energy source to move the plunger.

The device may further comprise a skin contact element configured to contact an injection site in use and movable from a first position to a second position, wherein movement of the skin contact element from the first position to the second position releases the first stored energy source.

The device may further comprise a needle safety mechanism configured to cover the needle, the needle safety mechanism being in a locked position, wherein either the movement of the needle assembly from the initial position to the insertion position or movement of the plunger through the drug containing portion releases the needle safety mechanism from the locked position.

In a fifth aspect of the invention, there is provided a drug delivery device comprising:
- a housing, including an external housing portion configured to be held in use and a drug containing portion containing a drug, and a plunger positioned within the drug containing portion, the drug containing portion having an outlet for dispensing the drug, wherein, in an initial position, the outlet is sealed;
- a needle assembly comprising a needle fixed to a needle hub, the needle hub configured to move relative to the drug containing portion from an initial position within the housing to an insertion position in which the needle extends beyond the housing;
- a drive mechanism comprising a stored energy source operable to apply pressure on the plunger or the drug container to pressurise the drug;
- a first release mechanism operable to move the needle hub and to unseal the outlet after the drug has been pressurised.

In a further aspect of the invention, there is provided a release mechanism for a stored energy source or other source of motive force, comprising: a live hinge, wherein the live hinge is in a folded state to retain the stored energy source and is allowed to expand to release the stored energy source. The live hinge effectively acts as a gearing mechanism to reduce the force required to retain the stored energy source. The release mechanism may be provided in a drug delivery device. Use of a live hinge in this manner provides an effective and low cost means to retain a high force.

It should be clear, that features of the invention described in relation to one aspect of the invention may be applied to other aspects of the invention.

BRIEF DESCRIPTION OF THE DRAWINGS

Embodiments of the invention will now be described in detail, by way of example only, with reference to the accompanying drawings in which:

FIG. 15 shows the device of FIG. 14 with the needle moved forward to an insertion position in which the needle extends beyond the skin contact element;

FIG. 16 is a cross-section perpendicular to the section of FIG. 15;

DETAILED DESCRIPTION

Figure 1:
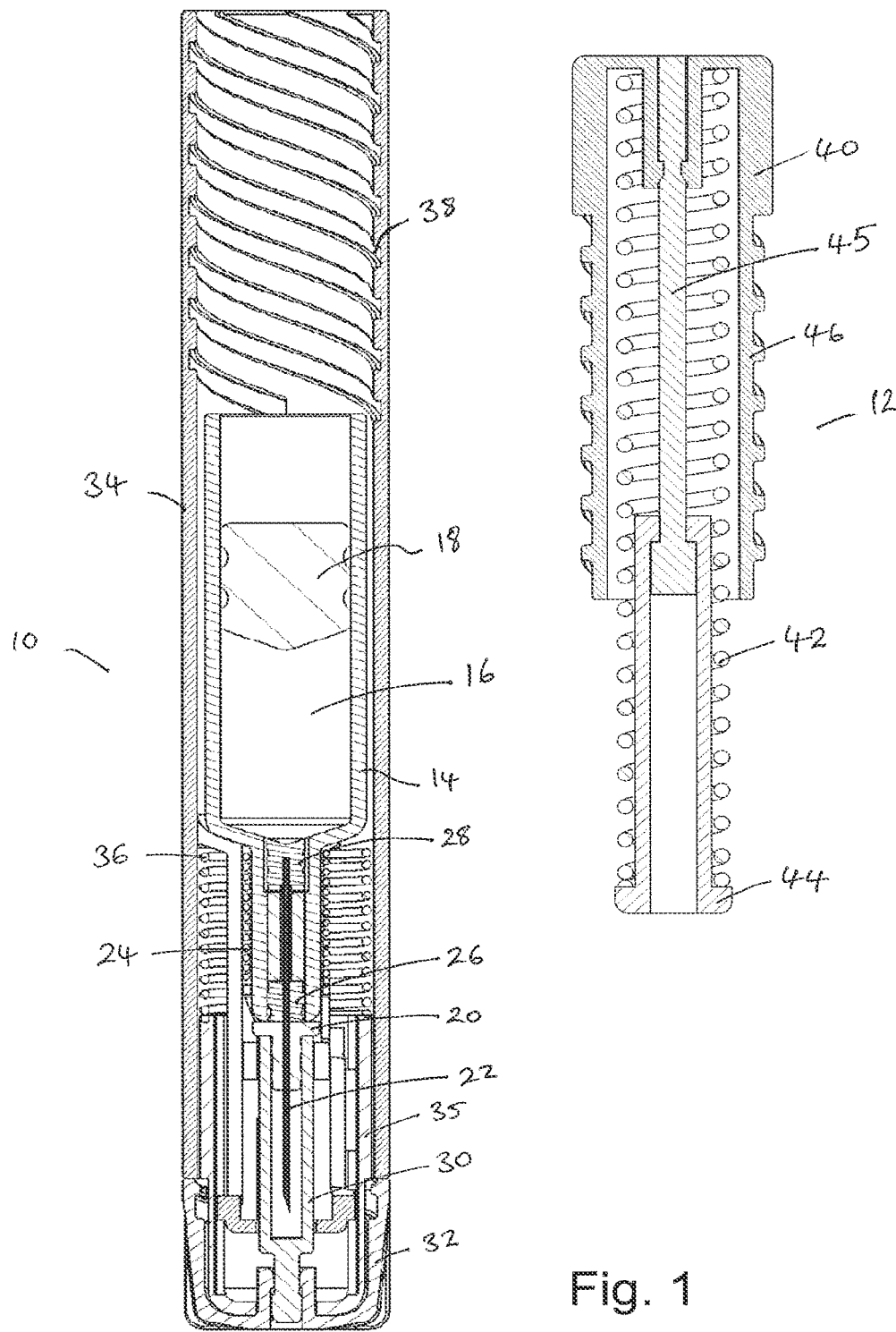
FIG. 1 is a schematic cross-sectional illustration of a drug delivery device in accordance with a first embodiment of the invention.

FIG. 1 is a schematic cross-sectional illustration of a drug delivery device in accordance with a first embodiment of the invention. The device comprises a first sub-assembly 10 having a drug container 14 and a needle insertion mechanism, and a second sub-assembly 12 comprising a reusable power pack. The first sub-assembly comprises a drug container 14 containing a drug 16, a plunger 18 within the drug container, a needle hub 20 securely holding a needle 22, and a needle insertion spring 24 positioned between the drug container and the needle hub. The drug container has an outlet that is sealed by a first sealing member 26, and through which the needle 22 passes. The first sealing member 26 is securely retained to the drug container by lobes on the drug container received in corresponding indents in the first sealing member. The distal end of the needle is sealed by a second sealing member 28. The drug 16 is able to pass the second sealing member 28 to flood the space between the first and second sealing members. A needle shield 30 covers the proximal end of the needle. The needle shield is coupled to the cap 32 so that it is removed with the cap. The cap couples to housing 34, which holds the drug container.

A skin contact element 35 is provided both to allow for the release of the needle insertion spring 24 when the skin contact element is pressed against an injection site, and to cover the needle after use, as will be described. The skin contact element is urged into a proximal position by skin contact element spring 36.

The second sub-assembly 12 comprises a pusher rod 44, a delivery spring 42 and a powerpack housing 40. The powerpack housing 40 has an external thread 46 that is received in internal thread 38 formed in housing 10, as shown in FIG. 2. The delivery spring is positioned between the powerpack housing and the pusher rod. A retaining shaft 45 is provided to retain the pusher rod to the rest of the second sub-assembly.

Figure 2A:
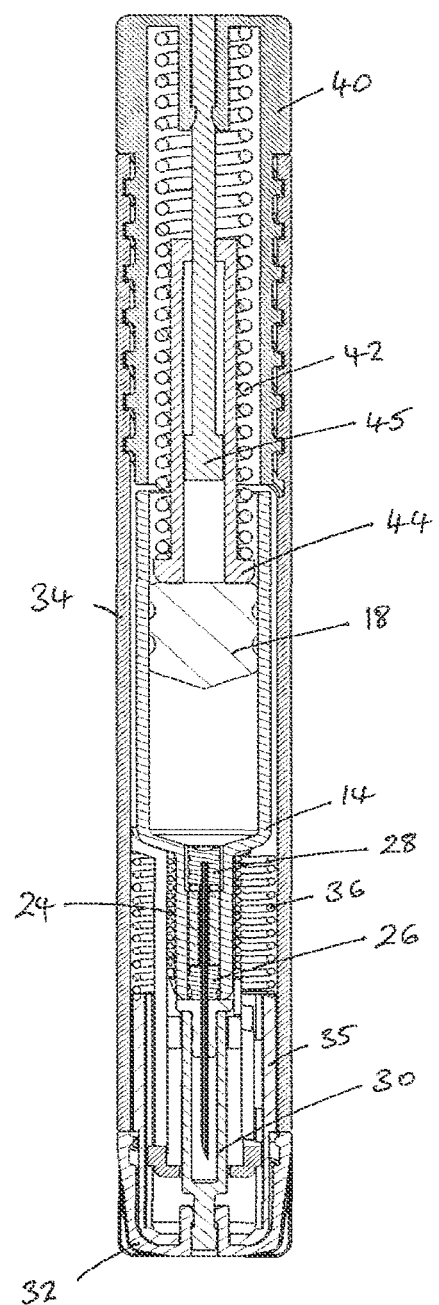
FIG. 2a is a schematic diagram illustrating the device of FIG. 1, prior to use, with the second sub-assembly screwed to the first sub-assembly to pressurise the drug in the drug container.
Figure 2B:
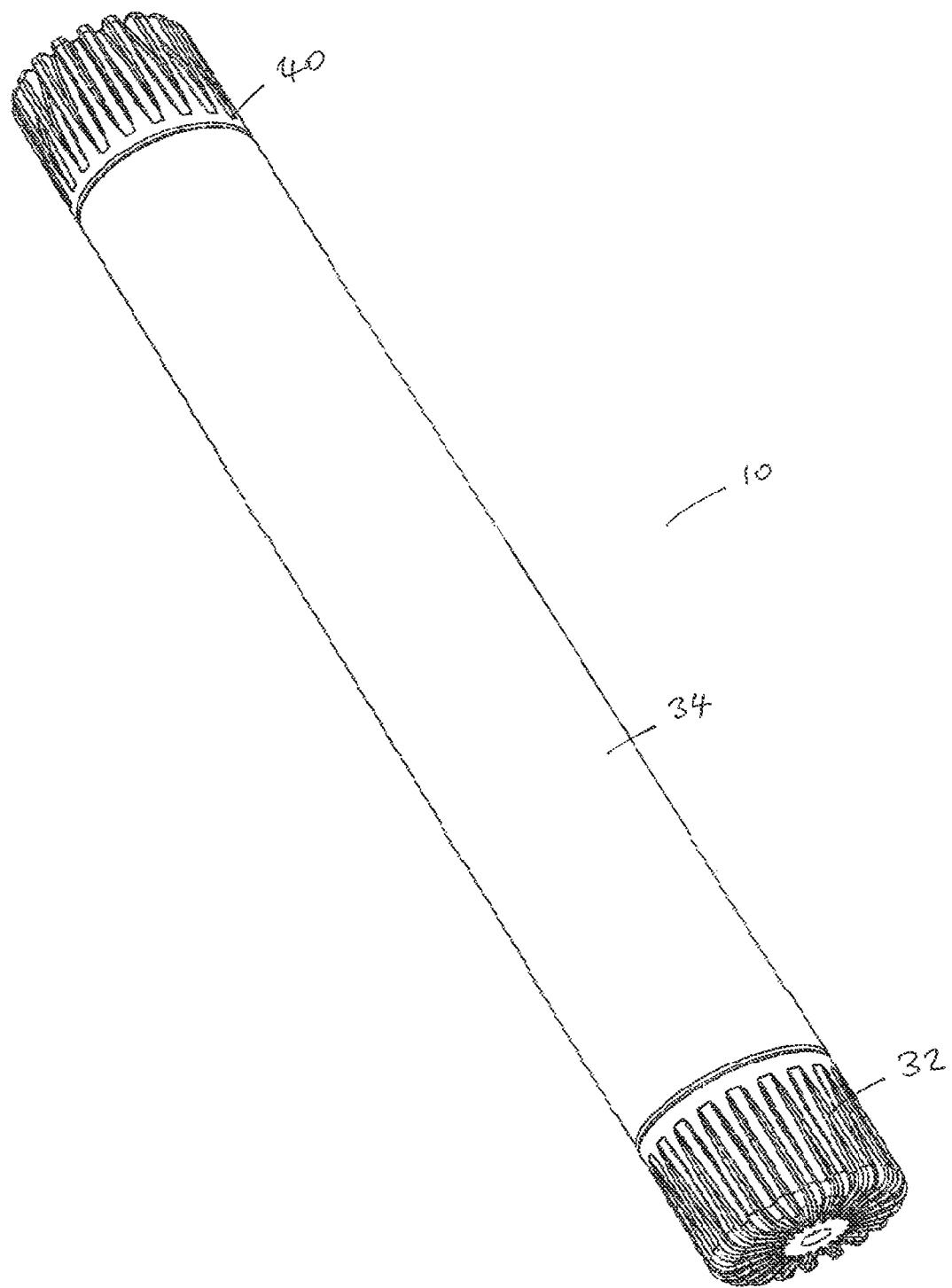
FIG. 2b is a perspective view of the device of FIG. 2a, prior to use.

FIG. 2a is a schematic diagram illustrating the device of FIG. 1, prior to use, with the second sub-assembly screwed to the first sub-assembly to pressurise the drug in the drug container. As the second sub-assembly is screwed onto the first sub-assembly, the pusher rod 44 abuts the plunger 18 and the delivery spring is compressed and pressurises the drug. The first and second sealing members prevent the delivery spring from expanding to urge the drug out of the drug container. FIG. 2b is a perspective view of the device of FIG. 2a prior to use.

Figure 3:
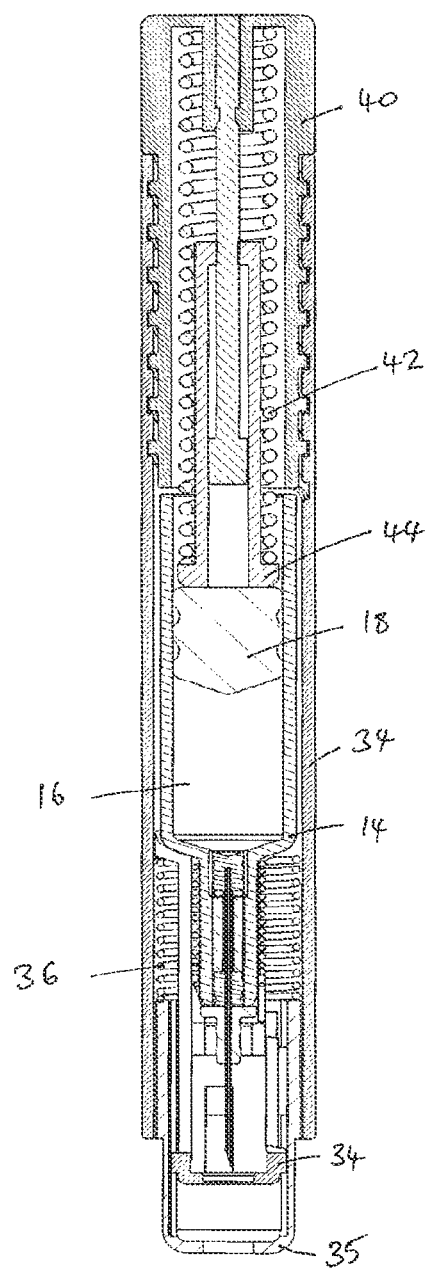
FIG. 3 shows the device of FIG. 2 with the cap removed.

FIGS. 3 to 7 show a sequence of operation of the device shown in FIGS. 1 and 2. FIG. 3 shows the device of FIG. 2 with the cap removed. When the cap 32 is removed from the housing, the needle shield 30 is removed with it.

Figure 4:
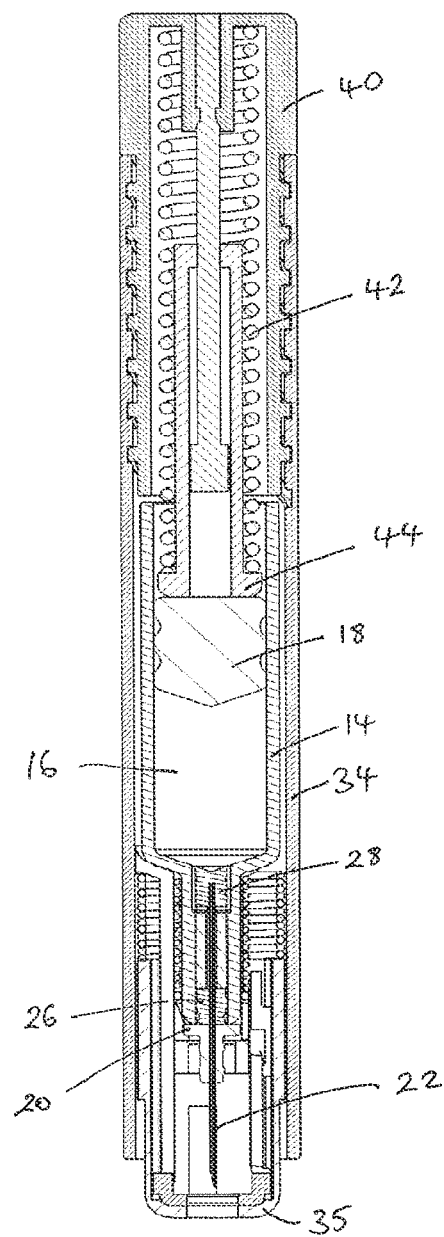
FIG. 4 shows cross-sectional and perspective views of the device of FIG. 3 with the skin contact element moved distally against the skin contact element spring.

FIG. 4 shows cross-sectional and perspective views of the device of FIG. 3 with the skin contact element 35 moved distally against the skin contact element spring 36, as it would be when pressed against an injection side. This releases the needle insertion mechanism, allowing the needle 22 to move forward to an insertion position.

Figure 9:
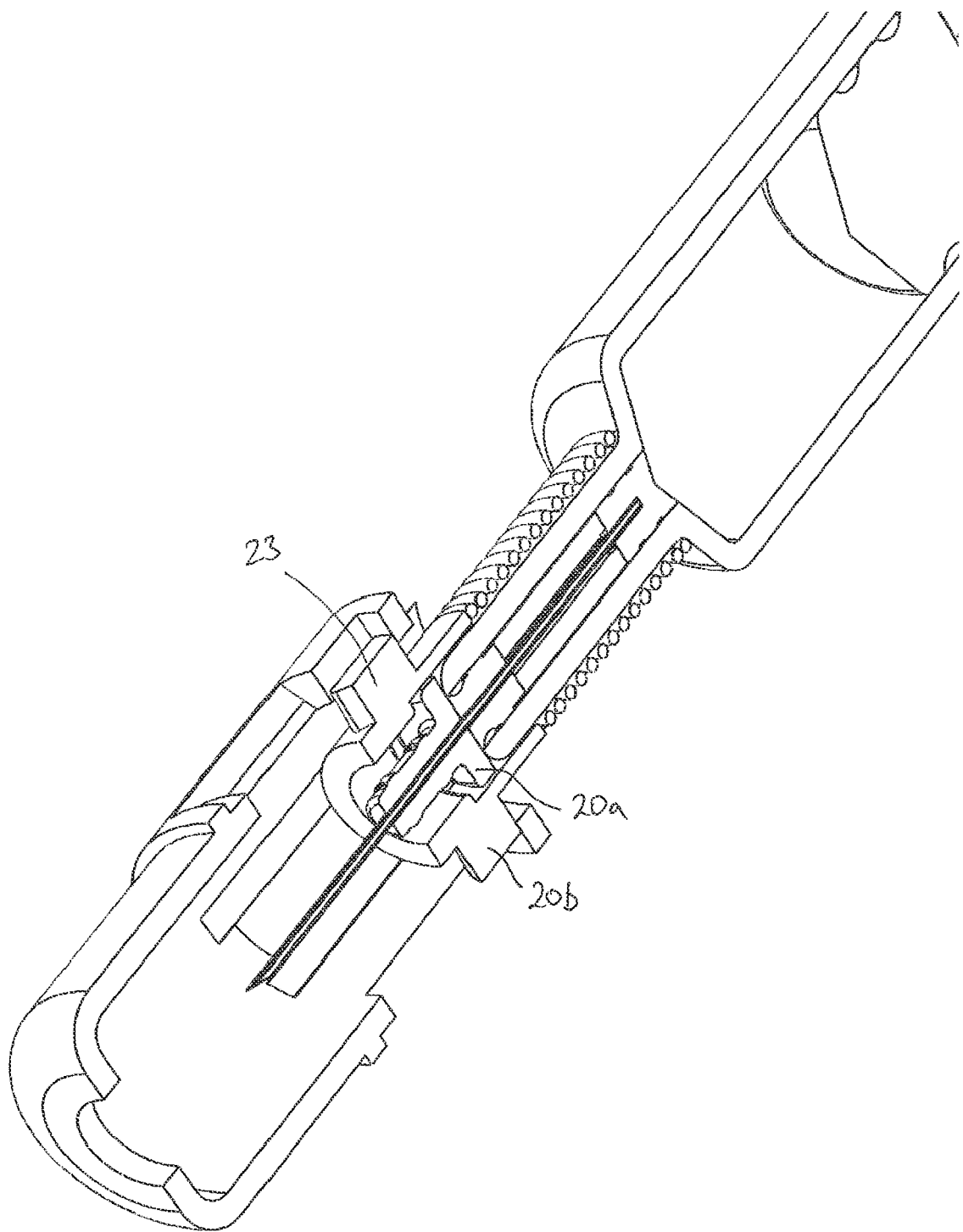
FIG. 9 is a perspective cross-sectional view of the needle insertion mechanism, with the housing and skin contact element spring removed.
Figure 10:
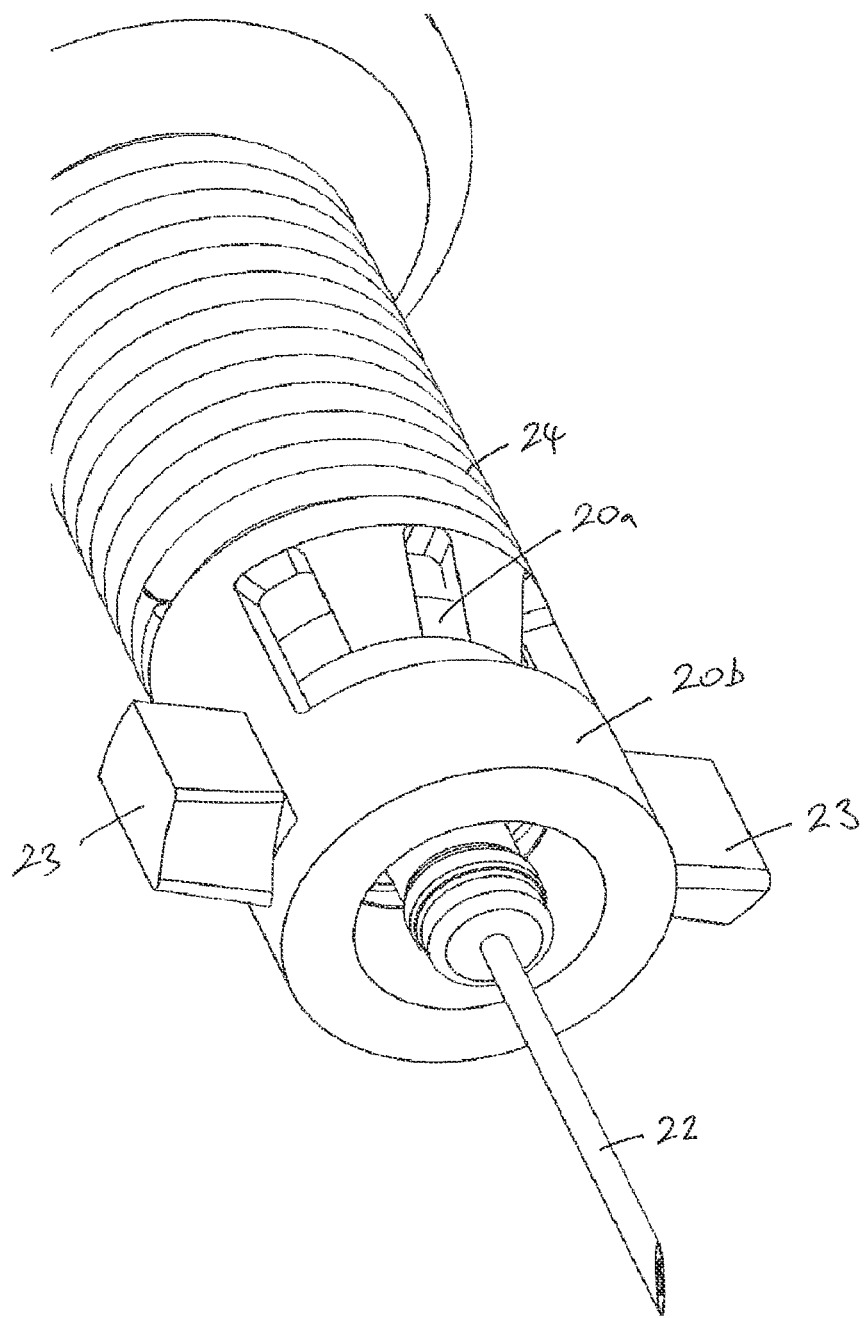
FIG. 10 is a perspective view of the needle hub.

FIG. 9 is a perspective cross-sectional view of the needle insertion mechanism, with the housing and skin contact element spring removed. The needle hub 20 comprises a central portion 20a fixed to the needle and rotatable portion 20b, which is free to rotate about the central portion 20a. In an initial position needle hub is constrained from forward movement by engagement of the wings 23 on the rotatable portion with the housing (not shown). The rotatable portion 20b is constrained from rotation by engagement of the wings 23 with a flange on the skin contact element. When the skin contact element is moved rearward by pressing it against an injection site, the wings on the rotatable portion are disengaged from the flange and can rotate into channels formed in the housing. The needle hub can then move forward to the insertion position. FIG. 10 is a perspective view of the needle hub and needle.

Figure 5:
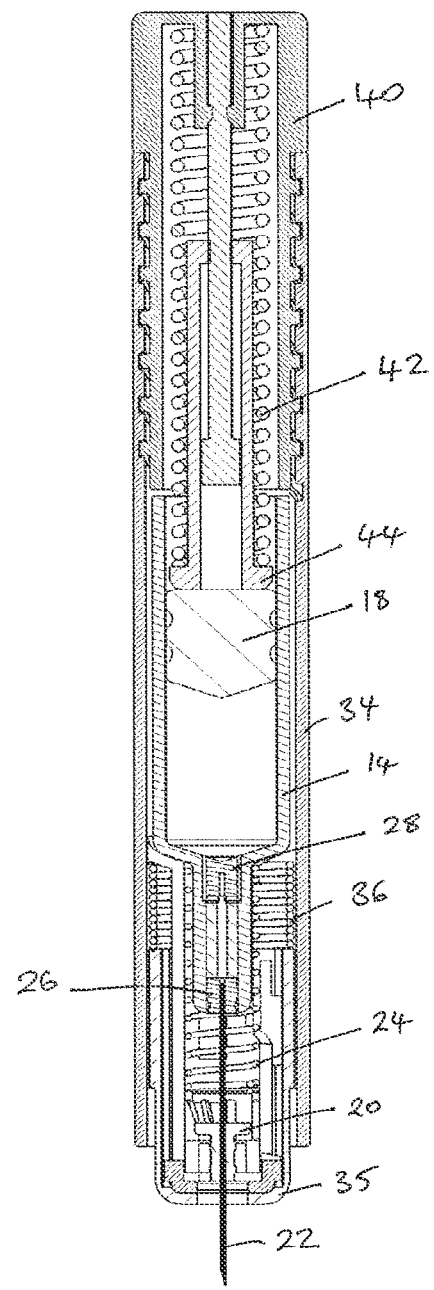
FIG. 5 shows the device of FIG. 4 with the needle insertion mechanism deployed.

FIG. 5 shows the device of FIG. 4 with the needle insertion mechanism deployed so that the needle is in an insertion position. In this position, the distal end of the needle 22 is moved out of engagement with the second sealing member 28 by the action of the needle insertion spring 24 on the needle hub 20, so that the drug can enter the distal end of the needle and pass to the injection site. The plunger is then urged in the proximal direction by the delivery spring 42. The needle 22 passes through the first sealing member 26 but a seal between the needle and the first sealing member is maintained to ensure that drug does not escape past the needle.

Figure 6:
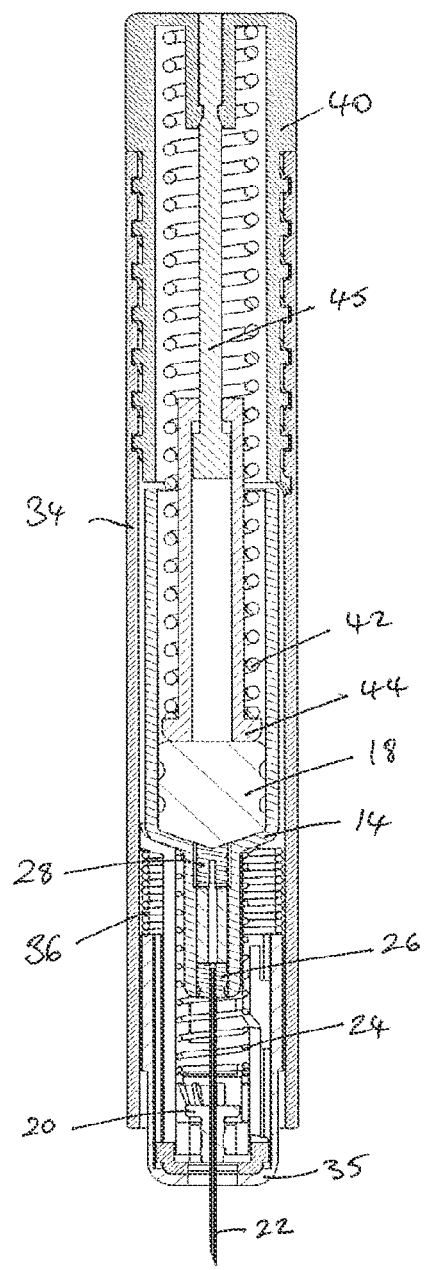
FIG. 6 shows the device of FIG. 5 with the plunger moved proximally through the drug container to delivery the drug through the needle.
Figure 7:
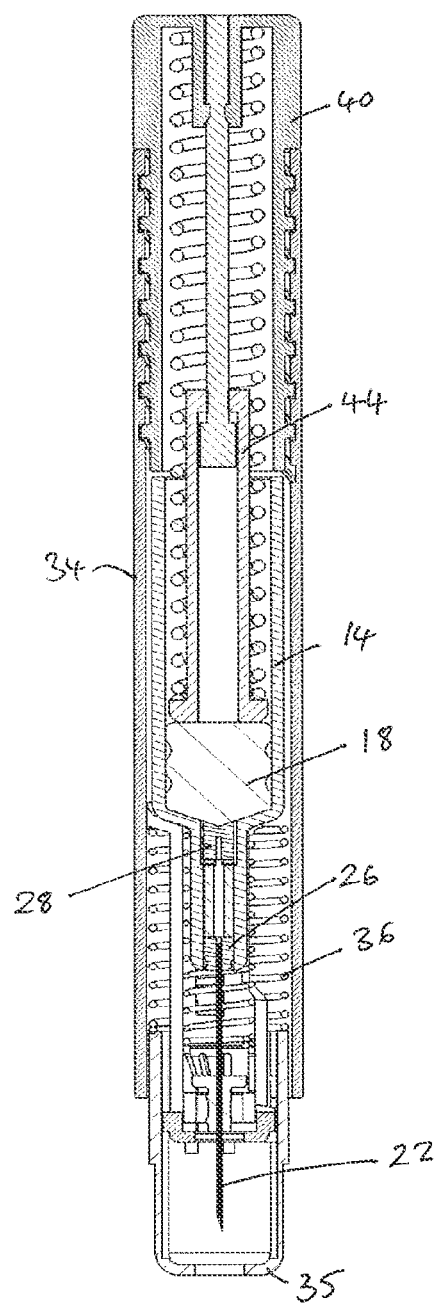
FIG. 7 shows the device of FIG. 6 with the skin contact element urged forward by the skin contact element spring to cover the needle following drug delivery.

In the position shown in FIG. 5, the drug can escape through the needle 20 into the injection site, allowing the compression spring 42 to expand and push the pusher rod forward. FIG. 6 shows the device of FIG. 5 with the plunger 18 moved proximally through the drug container 14 by the pusher rod 44 to deliver the drug through the needle 22. The device is then removed from the injection site and the skin contact element 35 is urged forward by the skin contact element spring 36 to cover the needle 22. FIG. 7 shows the device of FIG. 6 with the skin contact element 35 in the final, forward position. The skin contact element 35 is prevented from moving distally to expose the needle by the engagement of locking arms on the skin contact element abutting a locking surface on the housing 34.

Figure 8:
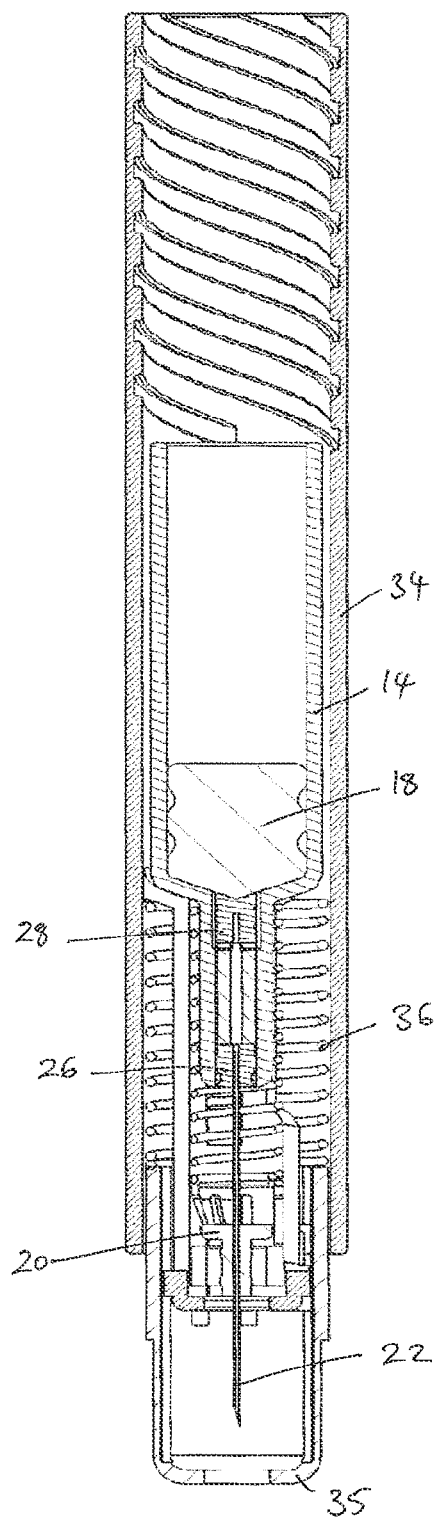
FIG. 8 shows the device of FIG. 7 with the second subassembly removed.

Following use, the second sub-assembly can be unscrewed from the first sub-assembly ready for use with a new first sub-assembly. FIG. 8 shows the device of FIG. 7 with the second sub-assembly removed. The first sub-assembly in this example is a single use, consumable item and after use can be safely disposed of.

Figures 11, 12:
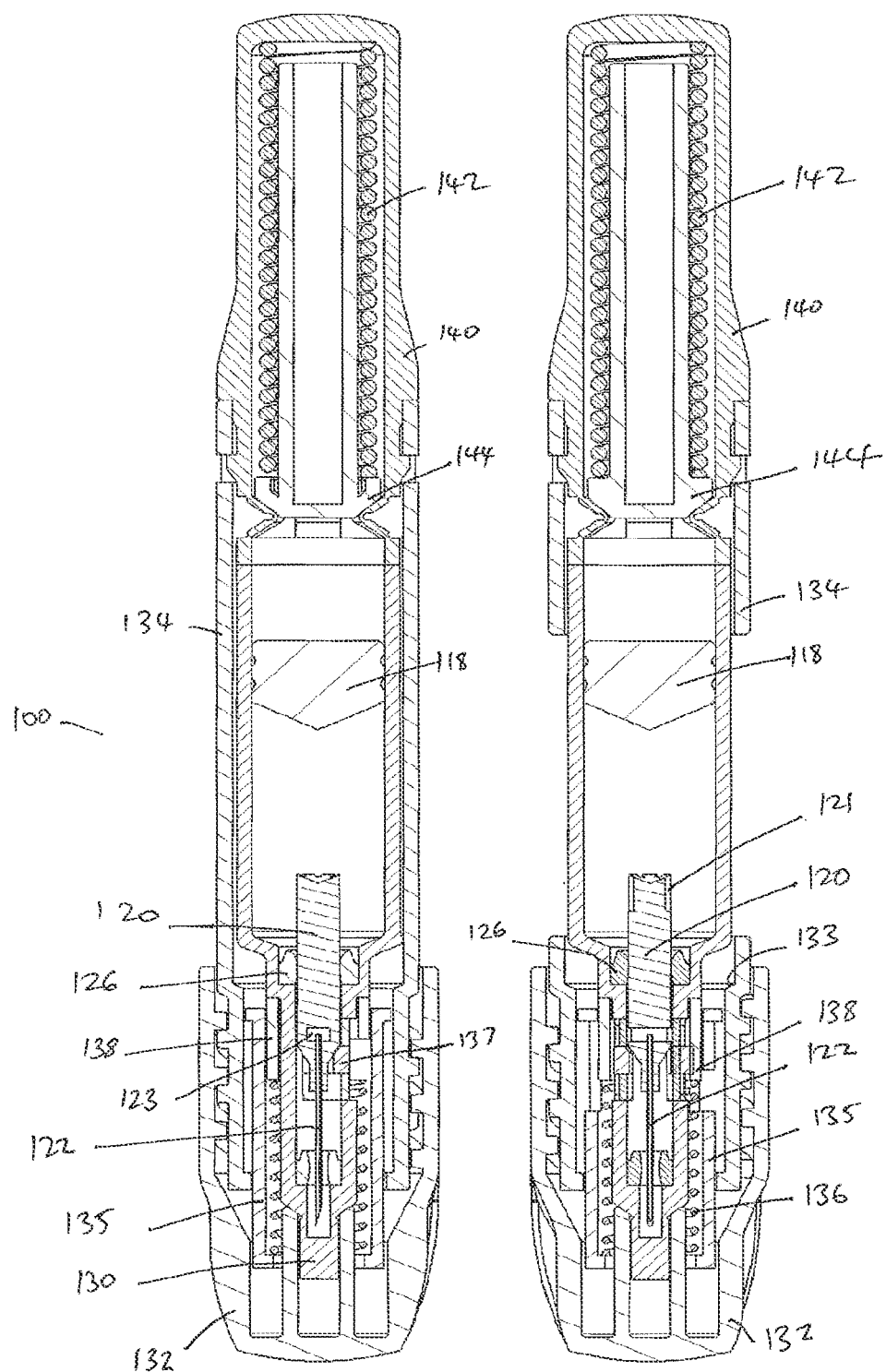
FIG. 11 is a cross-section of a second embodiment of the invention, before use.
FIG. 12 is a second cross-section of a second embodiment of the invention, before use, perpendicular to the section of FIG. 11.

FIG. 11 is a cross-section of a second embodiment of the invention, before use. In the embodiment of FIG. 11, the device includes a needle insertion mechanism that is driven by the pressure of the drug within the drug container.

The device 100 of FIG. 11 comprises a drug container assembly comprising a drug container 114 containing a drug 116 in liquid form or in solution and a plunger 118 provided within the drug container. An outlet of the drug container is sealed by a sealing member 126 and a needle hub 120. The sealing member is an annular, elastomeric sealing member that is compressed between the needle hub 120 and the drug container 114.

The needle hub 120 holds a hypodermic needle 122. A distal or rear end of the needle is positioned within a cavity 123 in the needle hub to allow drug to enter the needle, as explained below. A proximal or front end of the needle 122, in use, enters an injection site. A needle shield 130 is provided to cover the front end of the needle and keep it sterile before use.

Figure 19:
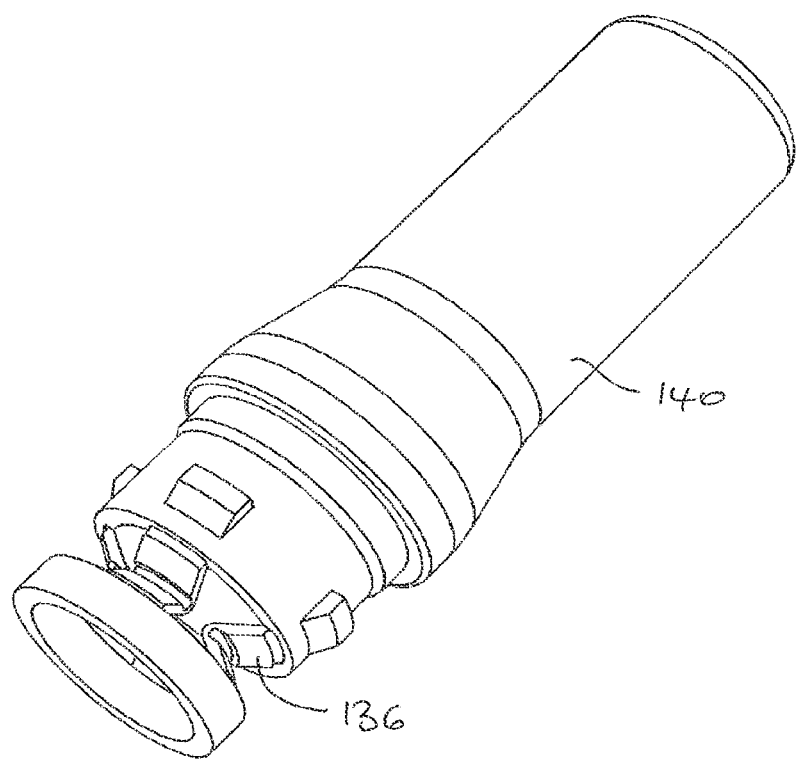
FIG. 19 is a perspective view of the hinge release mechanism.

The drug container assembly is held within a front housing 134. A drive mechanism is held within a rear housing 140, which is mechanically coupled to the front housing using a snap fit connection. The drive mechanism comprises a compression spring 142 and a pusher rod 144. The compression spring is held in a compressed state between the pusher rod 144 and the rear housing 140. The pusher rod 144 is prevented from forward travel by abutment with a flexible hinge mechanism 146. The flexible hinge mechanism abuts a rear end of the drug container 114. FIG. 19 is a perspective view of the rear housing illustrating more clearly the flexible hinges 146 used to retain the compression spring 142 in a compressed state and apart from the plunger 118. The drug container 114 is prevented from forward movement by abutment with cap 132 that is screwed onto the front housing 134.

FIG. 12 is a second cross-section of a second embodiment of the invention, perpendicular to the cross-section of FIG. 11. It can be seen in FIG. 12 that the needle hub 120 includes channels 121 in its rearward end.

The needle hub 120 is prevented from forward movement by abutment with a retaining arm 137 formed as part of the drug container. The retaining arm is a cantilever arm and is deflected inward to engage the needle hub 120 by a retaining component 138 positioned between the retaining arm and a skin contact element 135.

A skin contact element spring 136 is positioned between the skin contact element 135 and the retaining component 138 to bias the skin contact element into a forward position.

Figure 13:
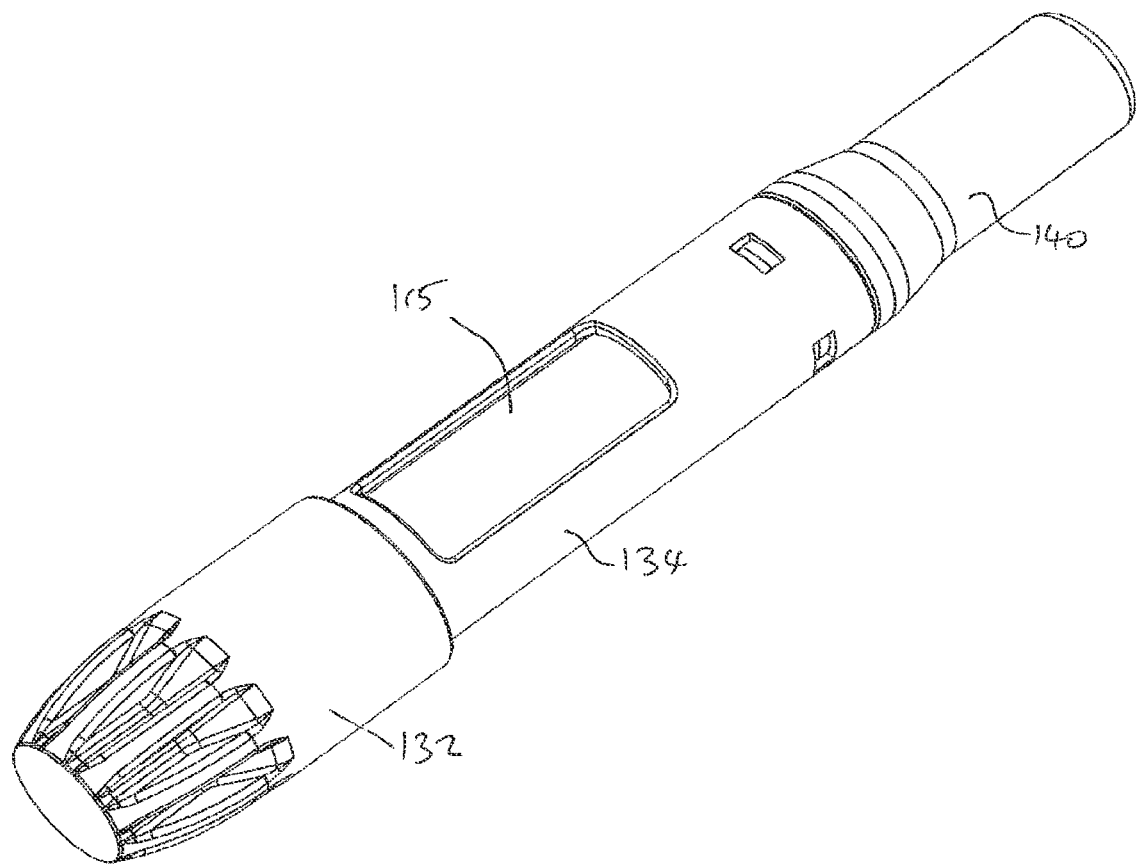
FIG. 13 is a perspective view of the device shown in FIG. 11.

FIG. 13 is a perspective view of the device shown in FIGS. 11 and 12. It can be seen that the front housing includes window portions 115 through the drug can be inspected.

Figure 14:
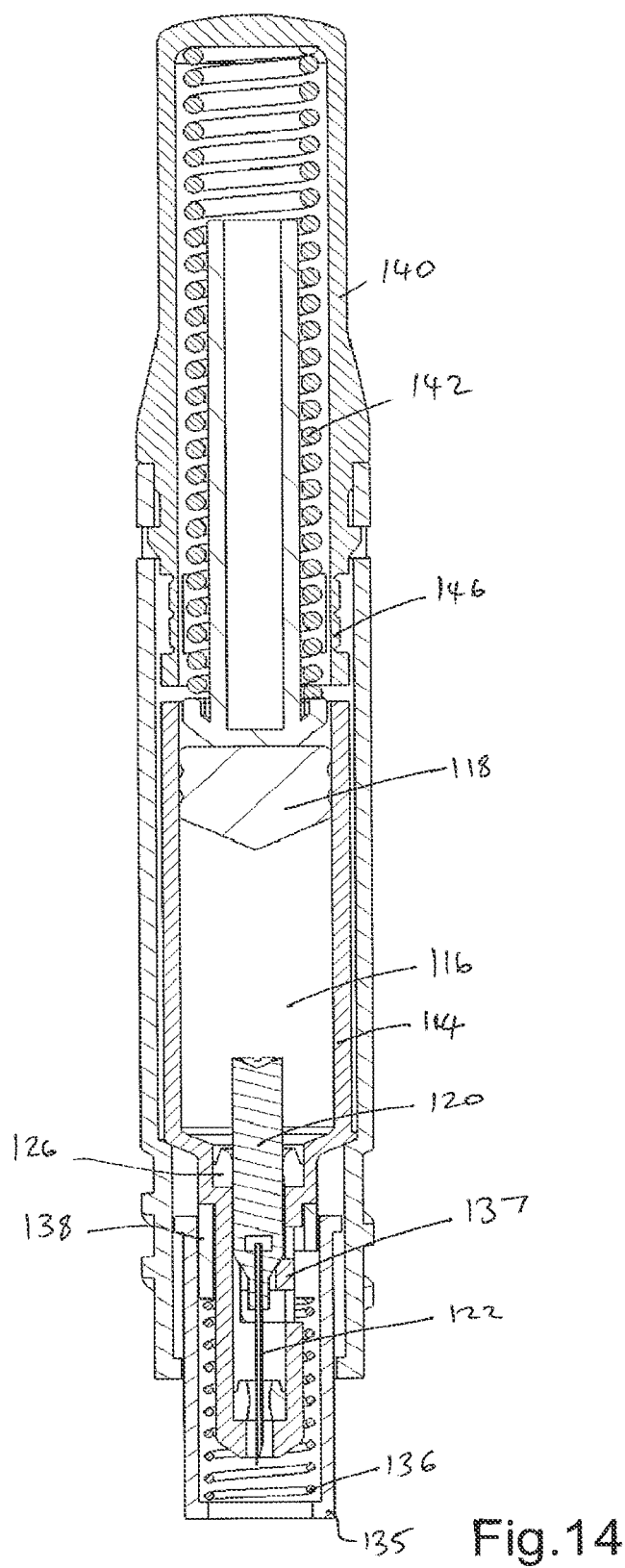
FIG. 14 shows the device of FIG. 11 with the cap 132 unscrewed from the front housing.

FIG. 14 shows the device of FIG. 11 with the cap 132 unscrewed from the front housing. The cap grips the needle shield 130 so that when the cap is unscrewed from the housing it pulls the needle shield 130 away with it. The needle shield 130 is integrally formed with the main body but a ring of weakness ensures that it breaks off in the desired manner.

Removal of the cap 132 also allows the drug container 114 to move forward within the front housing 134 until the front of the drug container abuts a ledge 133 formed in the interior of the front housing. This means that the hinge mechanism 146 can expand allowing the compression spring 142 to expand until the pusher rod contacts a rear surface of the plunger, as shown in FIG. 14. The compression spring 142 then acts to pressurise the drug 116, as the outlet remains sealed by the needle hub 120. The needle hub 120 is prevented from forward movement until the skin contact element 135 has been pressed against an injection site.

Figure 20:
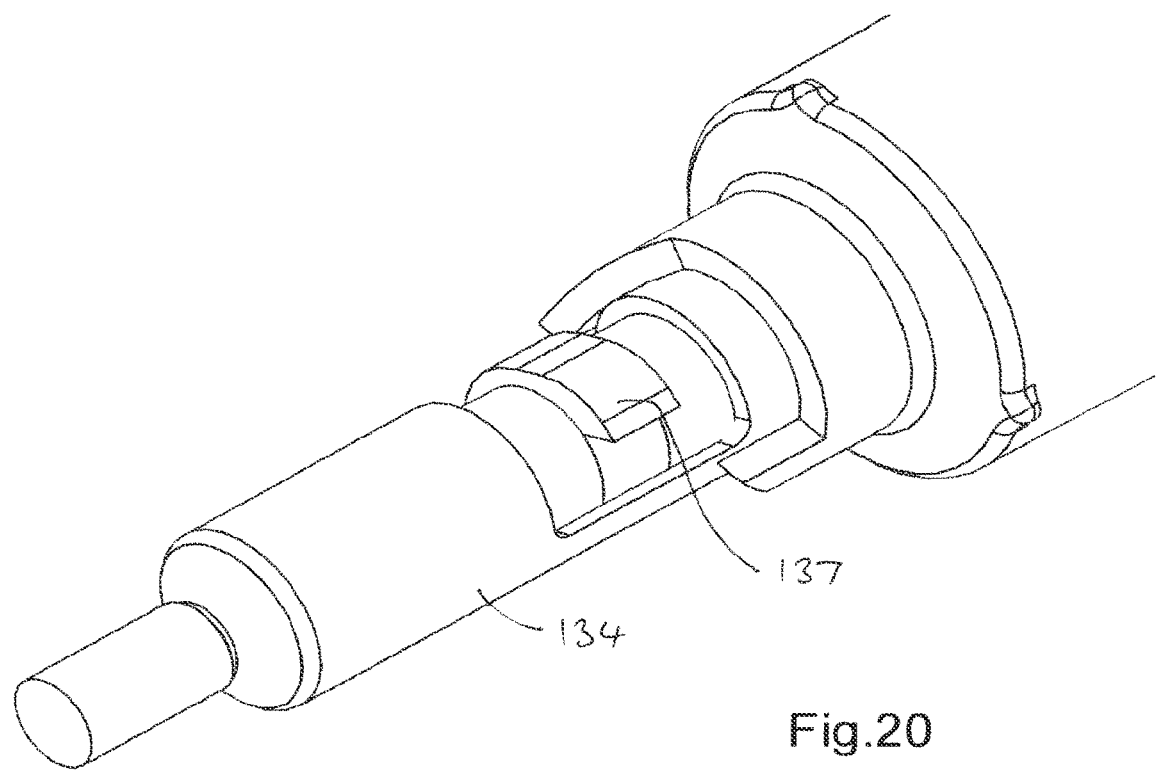
FIG. 20 is a perspective view of the front end of the drug container.
Figure 21:
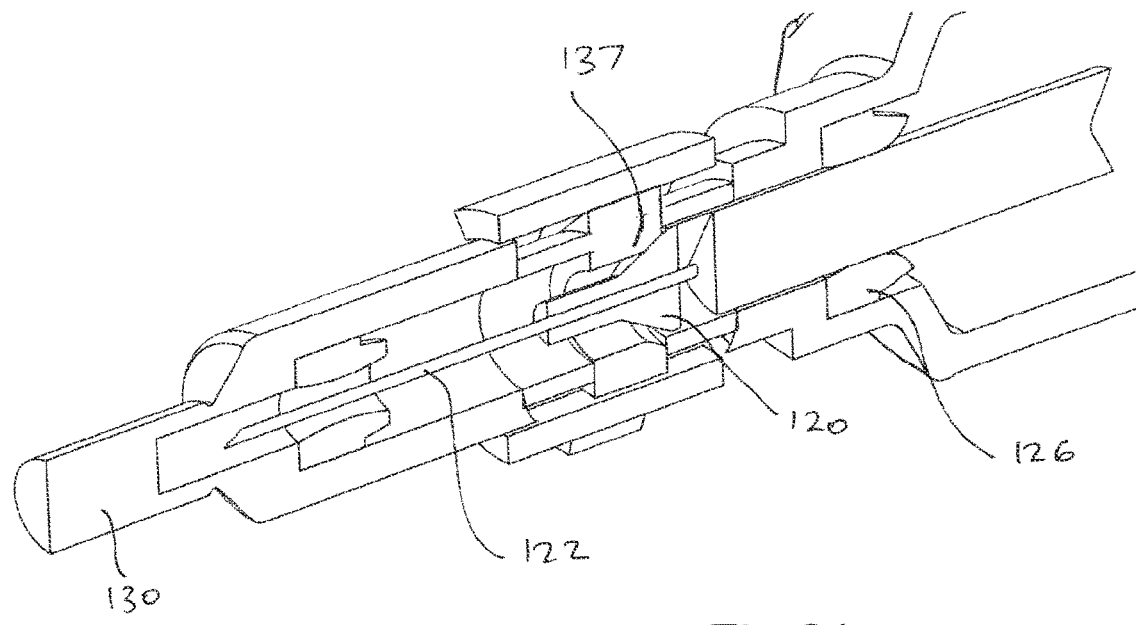
FIG. 21 is a cross-section showing the front end of the drug container and the retaining component.

When the skin sensor is pressed against the injection site it moves rearward relative to retaining component 138. This releases the retaining component 138 to rotate, under the action of the skin contact element spring 136 relative to the retaining arm 137 on the drug container. The rotation of the retaining component releases the retaining arm into a window in the retaining component, which in turn releases the needle hub for forward movement to an insertion position. FIG. 20 is a perspective view of the front end of the drug container 114, showing the retaining arm 137. FIG. 21 is a cross-section through the front end of the drug container and retaining component 138, showing the retaining arm 137 presses against the needle hub by the retaining component 138.

FIG. 15 shows the device of FIG. 14 with the needle moved forward to an insertion position in which the needle extends beyond the skin contact element. FIG. 16 is a cross-section perpendicular to the section of FIG. 15. The needle hub has been pushed forward to the point at which a front end of the needle hub engages a stopper in the front end of the drug container and the channels 121 extend through the sealing member to unseal the outlet and allow drug to pass the sealing member around the outside of the needle hub and into the distal end of the needle. The compression spring is then able to expand, pushing the drug out of the drug container and through the needle into the injection site.

Figure 17:
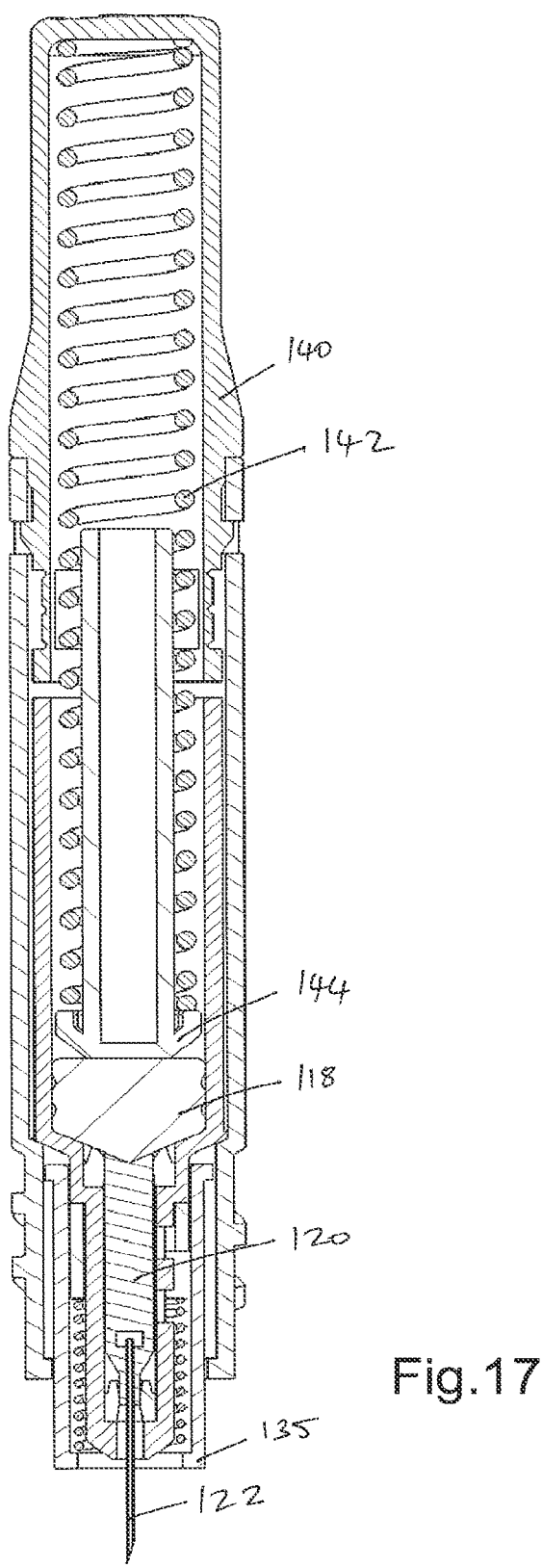
FIG. 17 shows the device of FIG. 15 with the plunger in a fully forward position.

FIG. 17 shows the device of FIG. 15 with the plunger in a fully forward position with the compression spring in an expanded condition. At this point, the drug has been delivered to the injection site.

Figure 18:
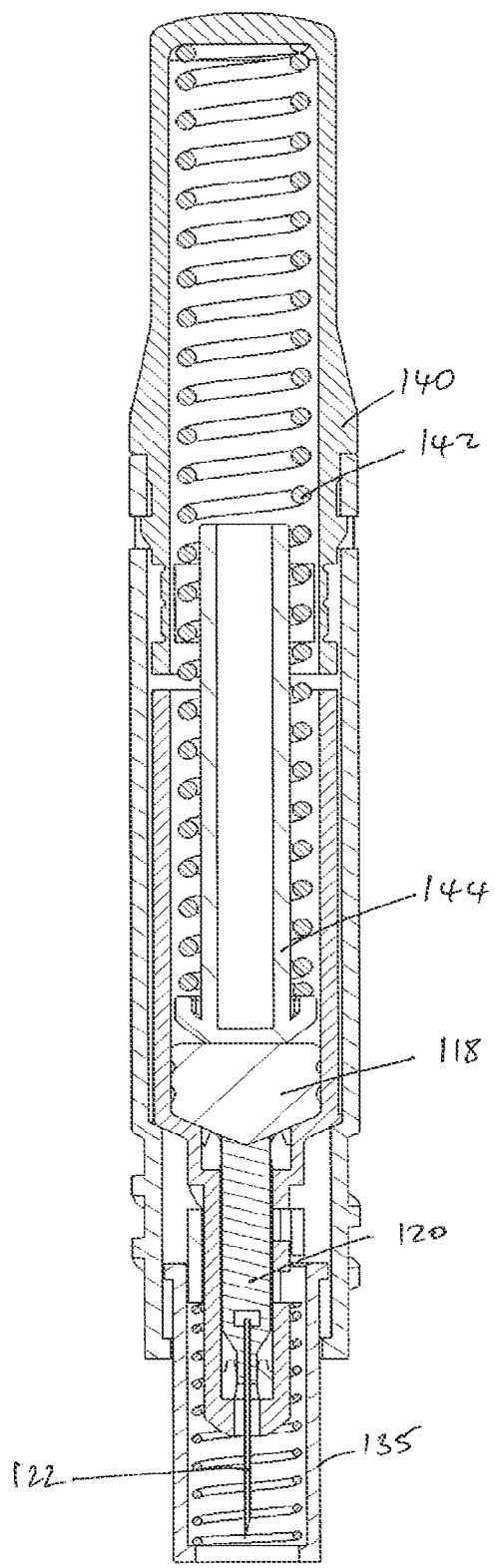
FIG. 18 shows the device of FIG. 17 when it has been withdrawn from the injection site.

FIG. 18 shows the device of FIG. 17 when it has been withdrawn from the injection site. The skin contact element spring has urged the skin contact element forward to cover the needle in order to reduce the chance of needle stick injury during disposal of the device.

Figure 22:
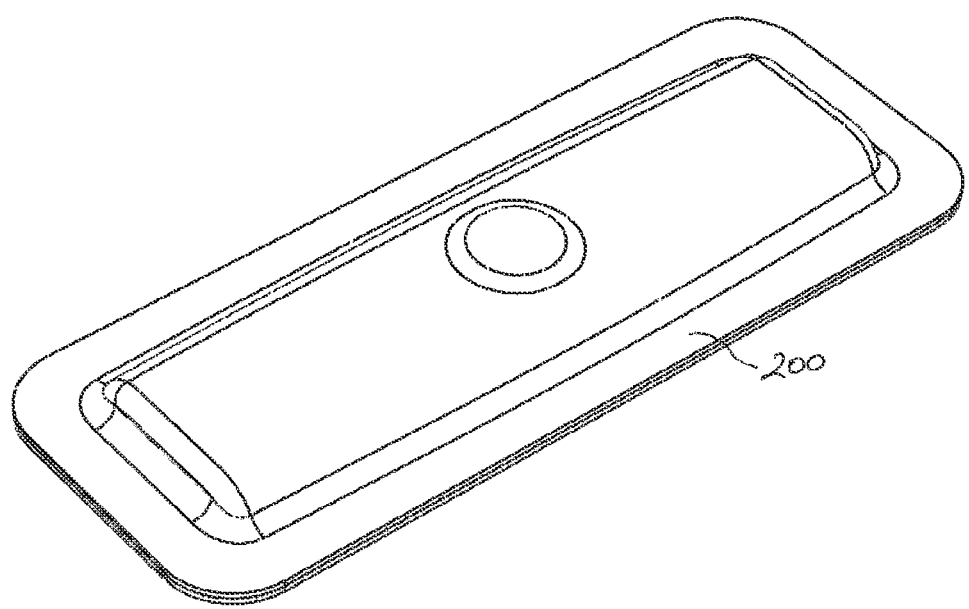
FIG. 22 is a perspective view of a third embodiment, within an exterior package.
Figure 23A:
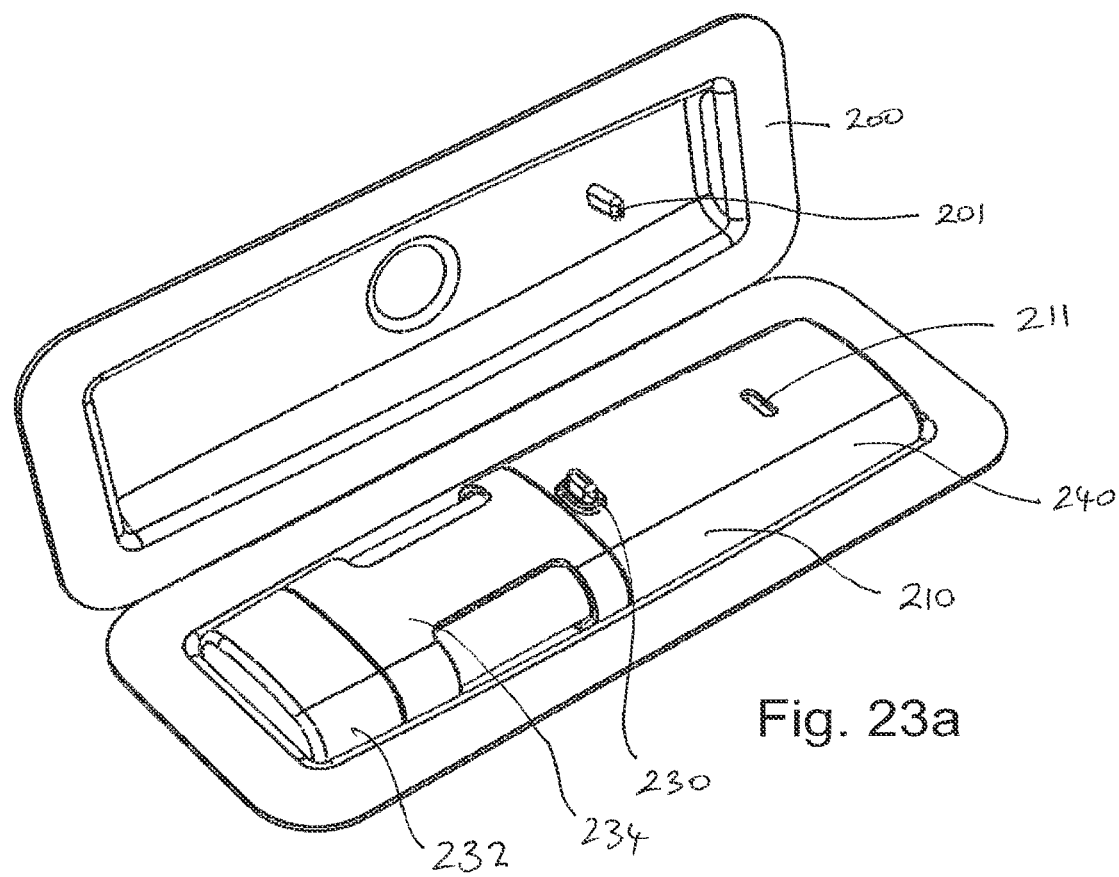
FIG. 23a shows the package of FIG. 22 in a open position.

FIG. 22 is a perspective view of a third embodiment, comprising a drug delivery device within an exterior package. The package 200 is a clamshell type package. FIG. 23a shows the package of FIG. 22 in a open position, revealing the drug delivery device. It can be seen that the package 200 includes an interior finger 201, which, when the package is closed, is received in an opening 211 in the device 210.

Figure 23B:
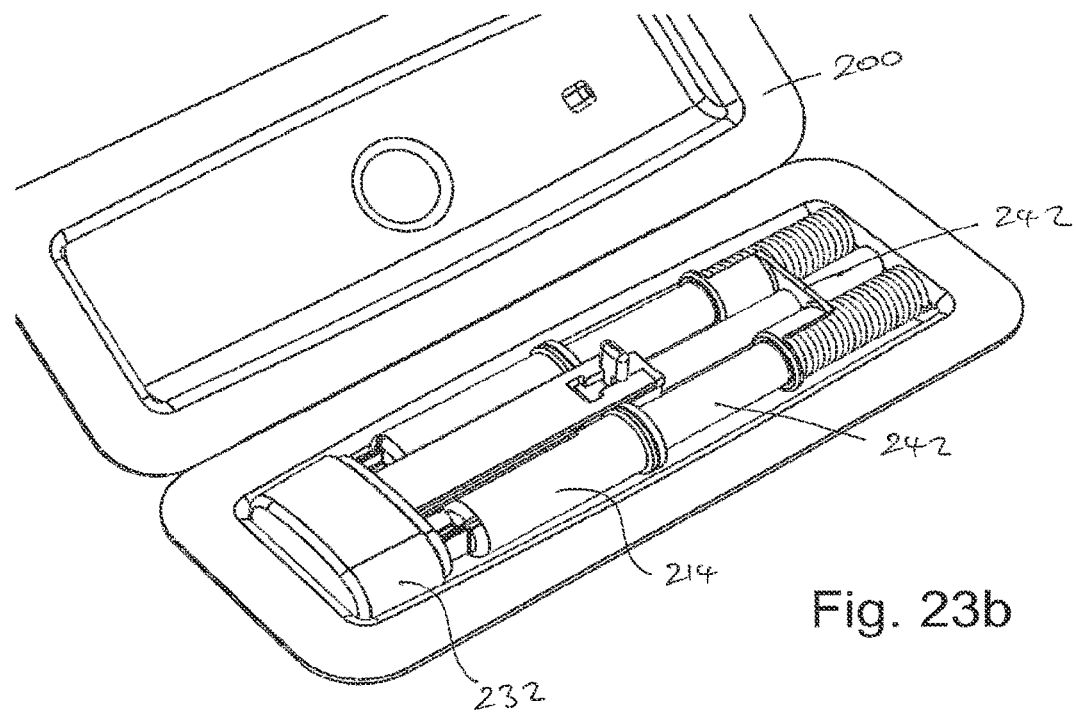
FIG. 23b shows the package and device of FIG. 23a, with the housing of the device removed for clarity.
Figure 23C:
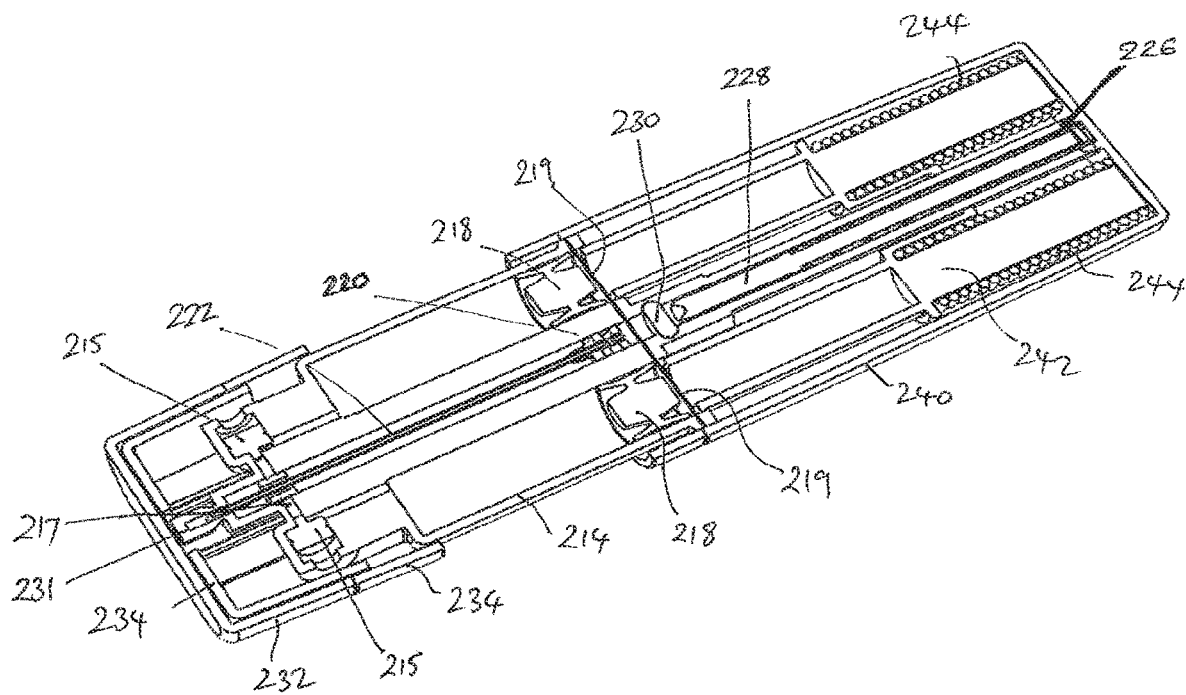
FIG. 23c is a perspective cross-sectional view of the device of FIG. 23b.

FIG. 23b is a view of the device of FIG. 23a, with the package and the housing of the device removed for clarity. The device comprises two separate drug containers, each of which provides drug to the same hypodermic needle. Each drug container has an associated drive mechanism. The drugs within each drug container may be the same or different to each other.

The drive mechanism comprises two compression springs 244 positioned between a rear housing 240 of the device and a central beam of a pusher element 242. When the package is closed, the finger 201 engages a front facing surface of the pusher 242 to prevent it moving forward under the influence of the compression springs.

It can be seen from FIG. 23b that the device comprises a front housing 234 and a rear housing 240. The front housing 234 includes two drug containers 214 each containing a drug. The drug containers each contain a cup seal type plunger 218, of the type described in WO2010/094916, and are sealed with a foil 219 at their rear ends.

The front housing also includes a needle assembly between the two drug containing portions. A needle assembly includes a hypodermic needle 222 fixed to a needle hub 220. A needle insertion spring 226 is provided in the rear housing between the rear housing and a needle pusher 228 to move the needle forwardly and into an injection site. The needle pusher is initially restrained from contacting the needle hub 220 by a button element 230.

The forward end of the needle 222 is covered by a needle cover 231 to keep it sterile prior to use. The needle cover 231 is engaged by the cap 232.

Figure 24:
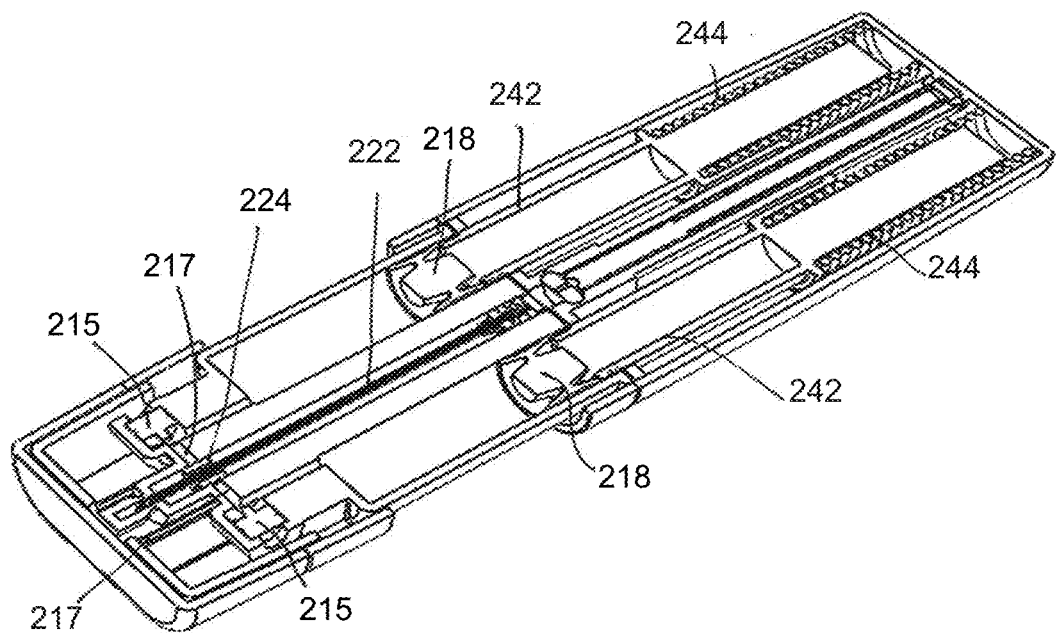
FIG. 24 shows the device of FIG. 23b, with the drive mechanism moved forward to pressurise the drugs.

FIG. 24 shows the device of FIG. 23b, with the pusher element 242 moved forward to pressurise the drugs. When the pusher element is released from the finger 201 as the package is opened, the pusher moves forward, breaking the foil seals 219 and contacting the plungers 218. The plungers retain the pusher because the drug cannot escape out of the drug containers until the drug containers are unsealed at the forward end.

The drug containers are initially sealed by separation sealing members 215. Separation sealing members 215 are elastomeric sealing members that seal exit conduits 217. The opposite ends of the conduits 217 are sealed by a first sealing element 224, which surrounds the needle 222.

Figure 25:
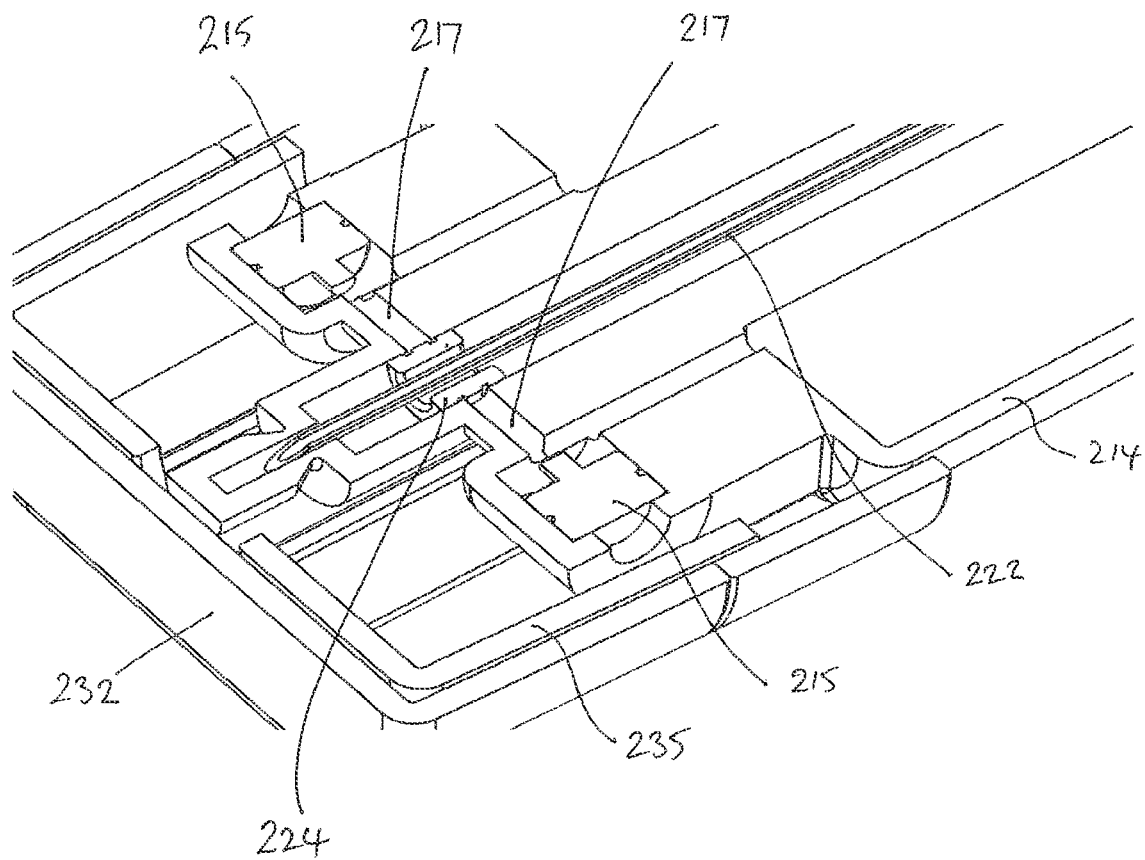
FIG. 25 shows in detail a front end of the device of FIG. 24.

When the pusher element contact the plungers 218, the pressure exerted by the drug on the separation sealing members forces them out of sealing engagement with the conduits 217 allow drug to pass into the conduits. The drug passes down a feed conduit to contact a front face of the separation sealing members and urges them away from the conduits 217. This position is shown in detail in FIG. 25.

Figure 26:
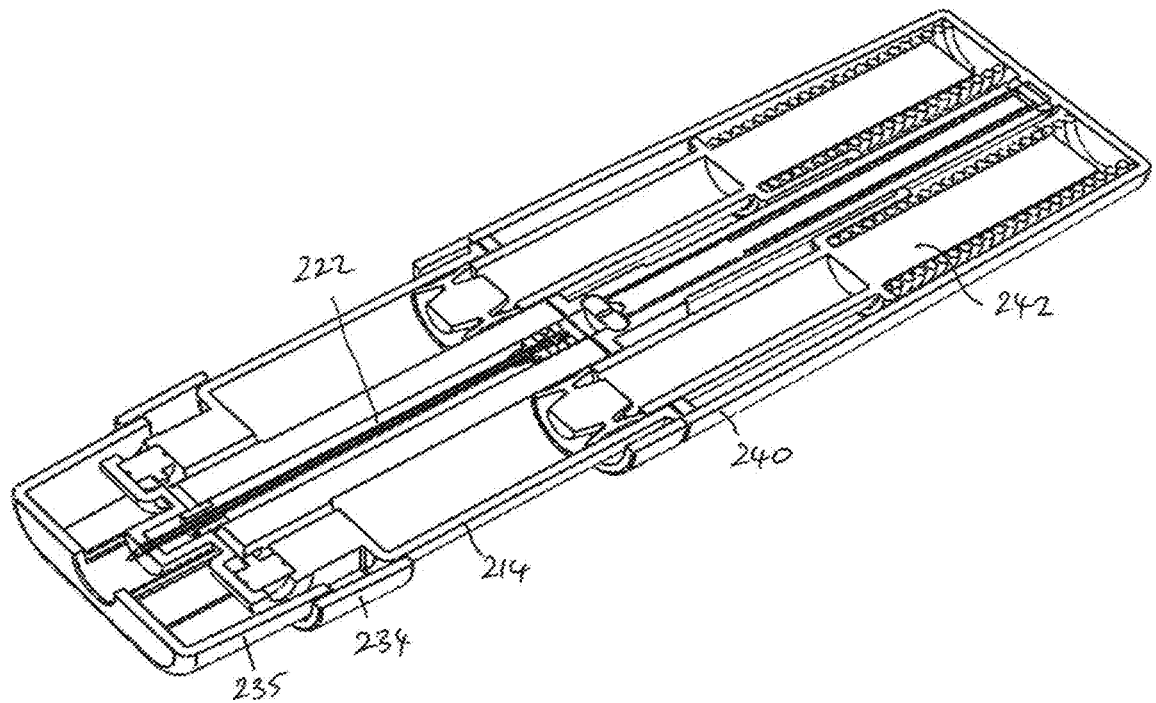
FIG. 26 shows the device of FIG. 24 with the cap removed.

Following removal of the device from the external package, the cap is pulled off by the user. The needle cover 231 is removed with the cap. This shown in FIG. 26.

The housing includes a skin contact element 235 that is biased into a proximal position by a biasing spring (not shown). The biasing spring is retained between the skin contact element and a portion of the drug containers. In operation the skin contact element 235 is pressed against the injection site and is moved against the biasing spring distally relative to the front housing.

Figure 27:
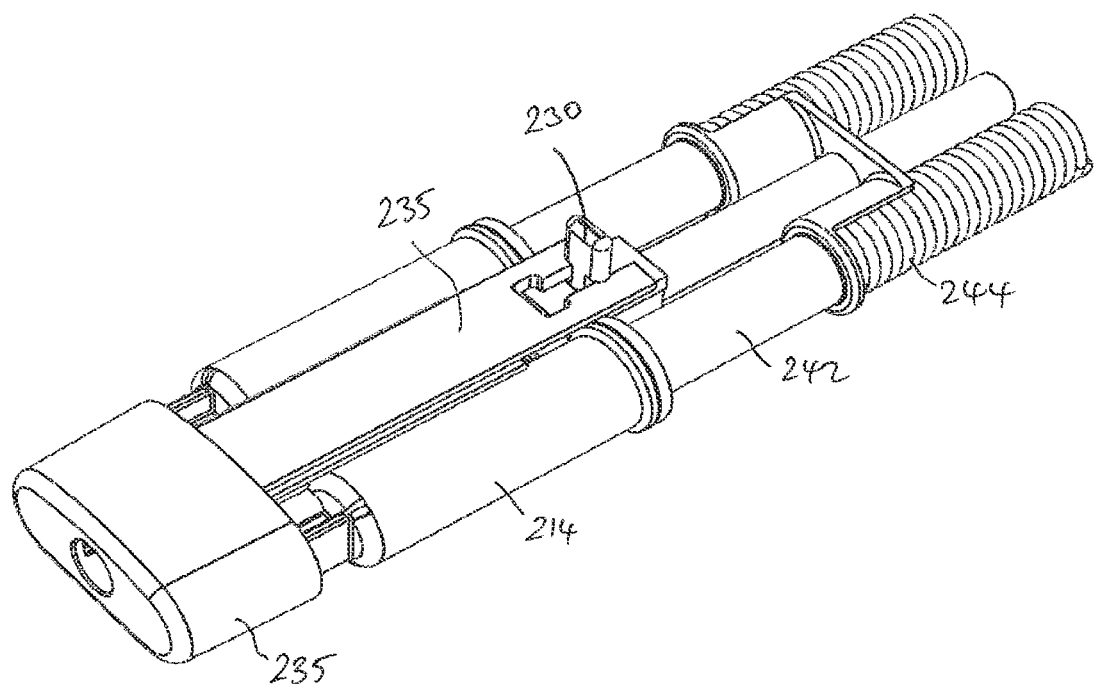
FIG. 27 shows the device with the housing removed, before the skin contact element is moved rearward.

The action of pressing the skin contact element against the injection site releases the button 230 that allows for the needle insertion mechanism to operate. FIG. 27 shows the device with the housing removed, before the skin contact element 235 is moved rearward. It can be seen the button 230 is prevented from being depressed by a portion of the skin contact element 235.

Figure 28:
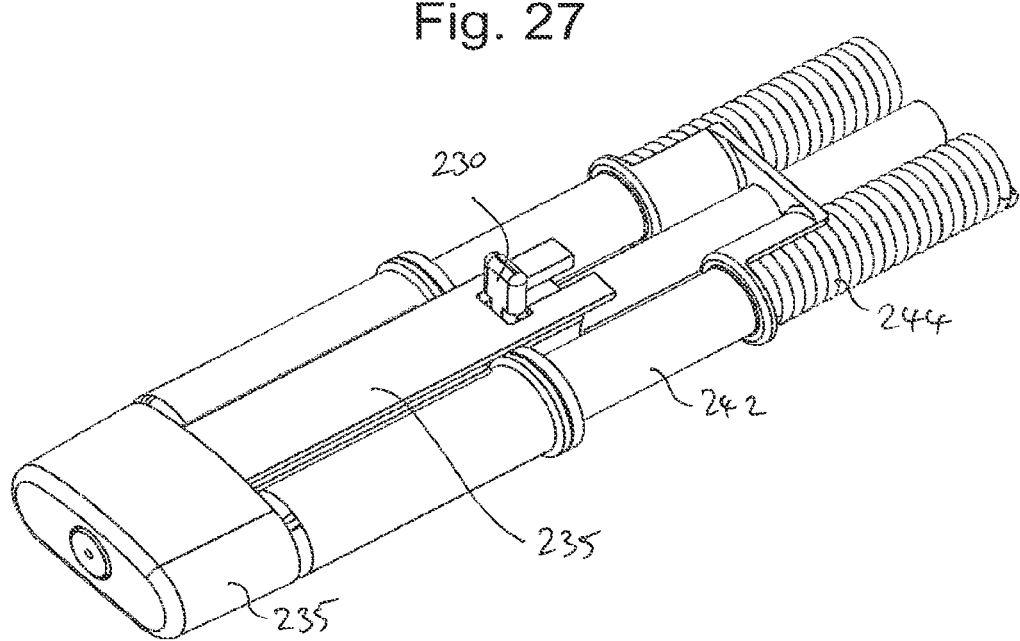
FIG. 28 shows the device of FIG. 27, with the skin contact element moved rearward.
Figure 29:
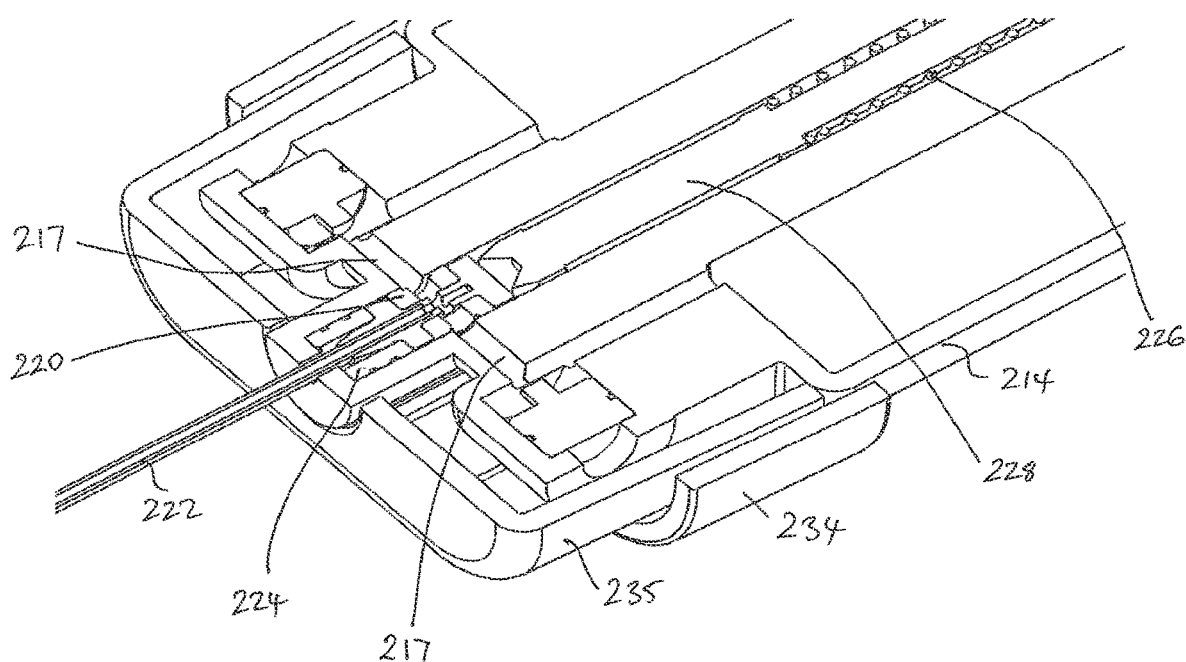
FIG. 29 shows the front part of the device with the needle in an insertion position.
Figure 30:
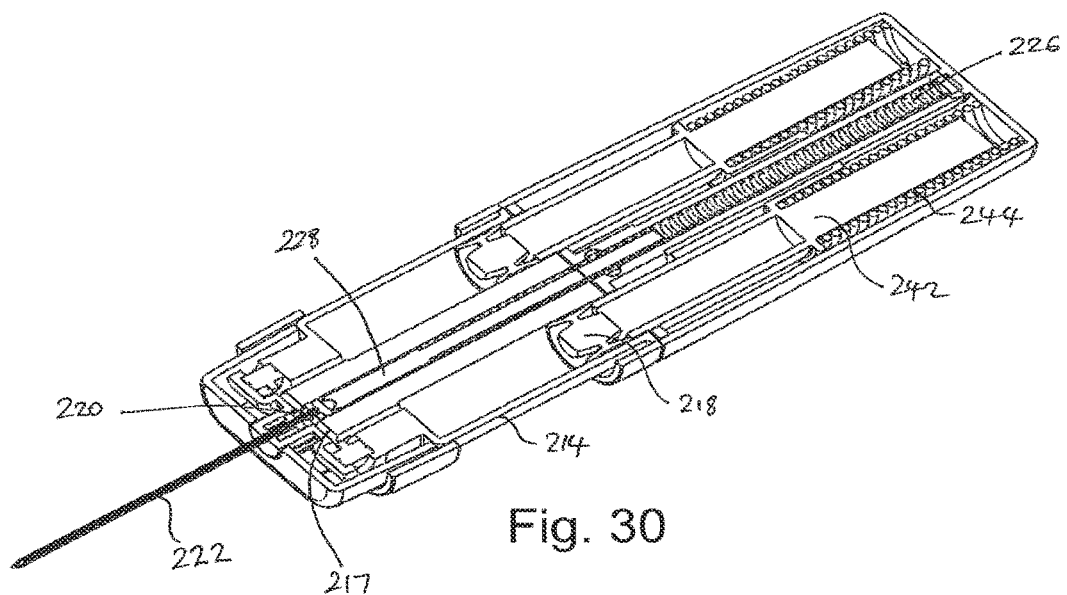
FIG. 30 shows the device with the needle in an insertion position.

FIG. 28 shows the skin contact element moved rearward to a position in which the button 230 is aligned with an opening in the skin sensor so that it can be depressed by the user. In this position, to activate needle insertion, the user depresses the button 230. This releases the needle pusher 228 for forward travel to engage the needle hub 220. The needle insertion spring 226 pushes the needle hub forward to the position shown in FIG. 30. In this position, the first sealing element 224 has been pushed forward by the needle hub and a conduit in the needle hub is aligned with the conduits 217. This is shown in detail in FIG. 29. The drugs in the drug containers can now pass into the rear end of the needle to the injection site.

Figure 31:
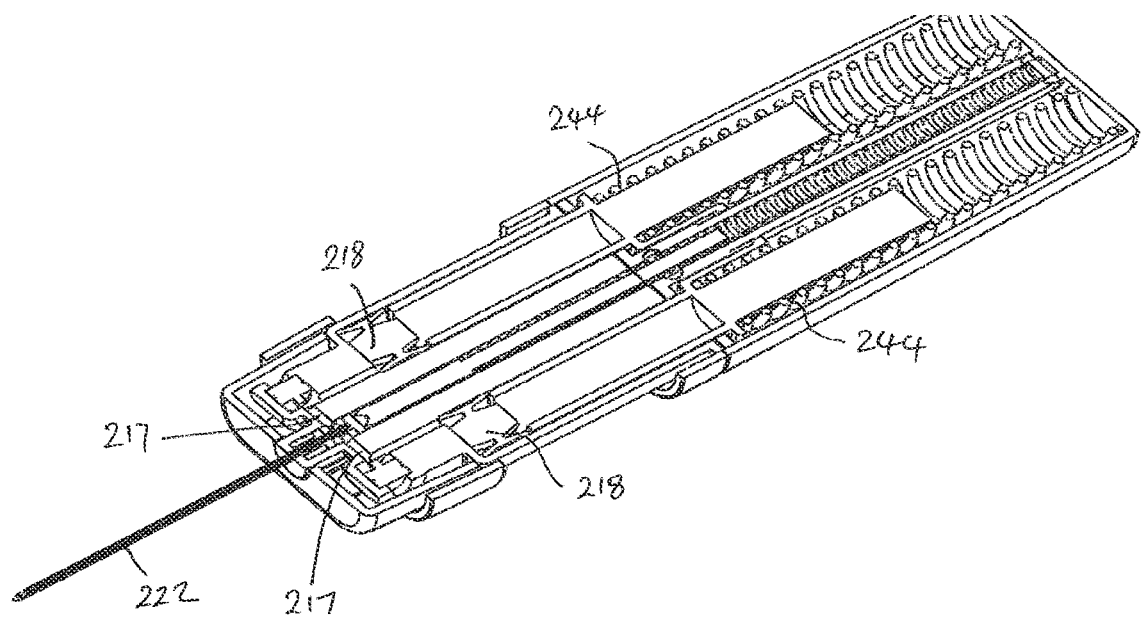
FIG. 31 shows the device with the plungers moved forward to deliver the drugs.

FIG. 31 shows the device after the plungers 218 have been moved through the drug containing portions by the expansion of the compression springs 244. The drug has been pushed through conduits 217 and out through the needle 222 into the injection site.

Figure 32:
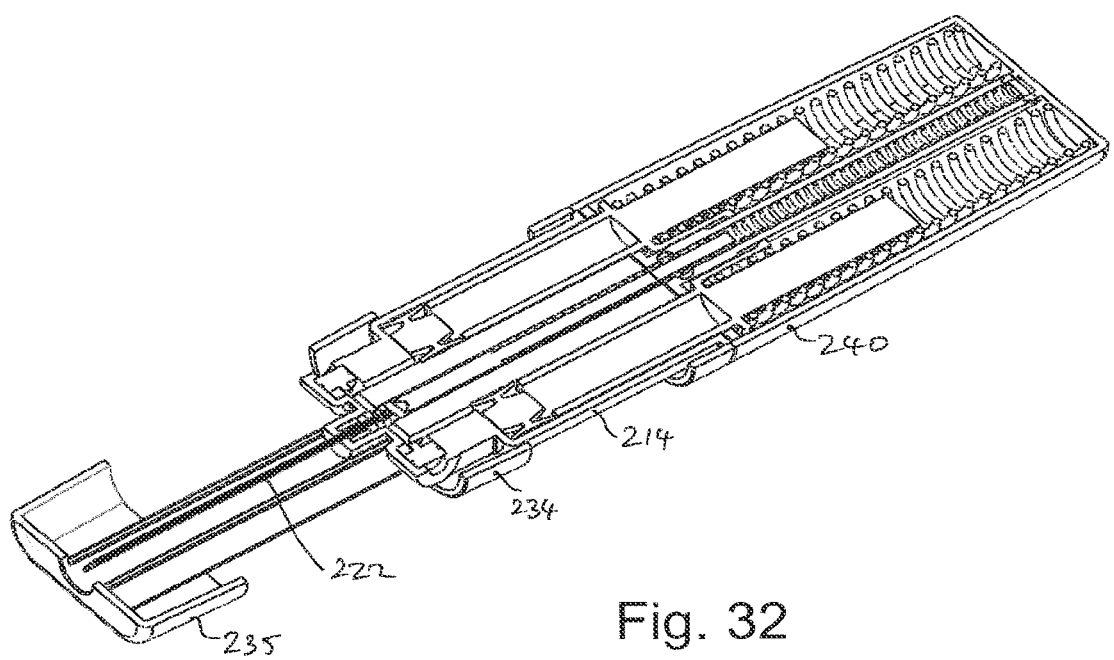
FIG. 32 shows the device with the skin contact element moved forward to cover the needle after use.

FIG. 32 shows the device after it has been removed from the injection site. The skin contact element 235 is moved to a proximal position covering the needle 222 owing to the action of the biasing spring. The skin contact element thereby provides a needle cover to prevent needle stick injuries following use of the device.

In the third embodiment described with reference to FIGS. 22 to 32, the plunger moves parallel to the direction of needle insertion. However, this does not need to be the case. It may be desirable to arrange the drug container such that the plunger moves at an angle to the direction of needle insertion. For example, the drug container may be arranged so that the plunger moves in a direction perpendicular to the direction of needle insertion.

In the third embodiment described with reference to FIGS. 22 to 32, there are two drug containing portions. However, it is possible to have more than two drug containing portions. It is also possible to have a drug containing portion that has an annular cross section and surrounds the needle assembly holding portion, with a single annular plunger and a single annular drive spring.

The embodiments described so far have all included an automatic needle insertion mechanism. However, it is possible to construct a device in accordance with the invention that has a manual needle insertion mechanism. In a manual needle insertion mechanism it is the action of the user pressing the device onto the injection site that inserts the needle. The skin contact element withdraws to expose the needle. The skin contact element may interact with the needle hub to unseal the outlet of the drug container as the needle reaches a fully inserted position. For example, a cam surface on the skin sensor may push a cam surface on the needle hub, forcing it to rotate to open the outlet. The needle hub may be constructed so that the needle itself does not rotate. A component of the needle hub may be provided that is free to rotate relative to the needle.

Figure 33:
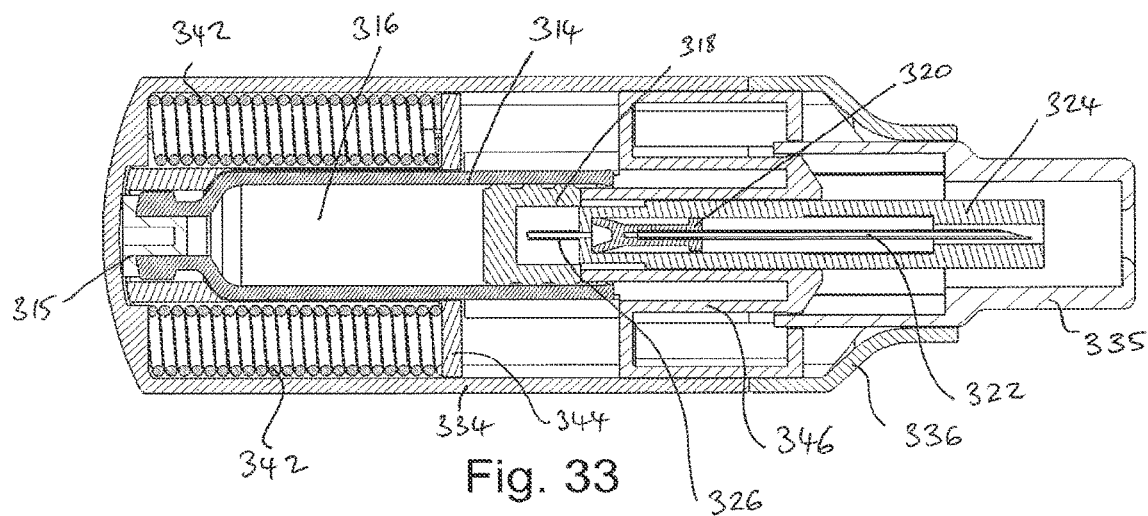
FIG. 33 is a cross-section of a fourth embodiment of the invention, prior to use.
Figure 34:
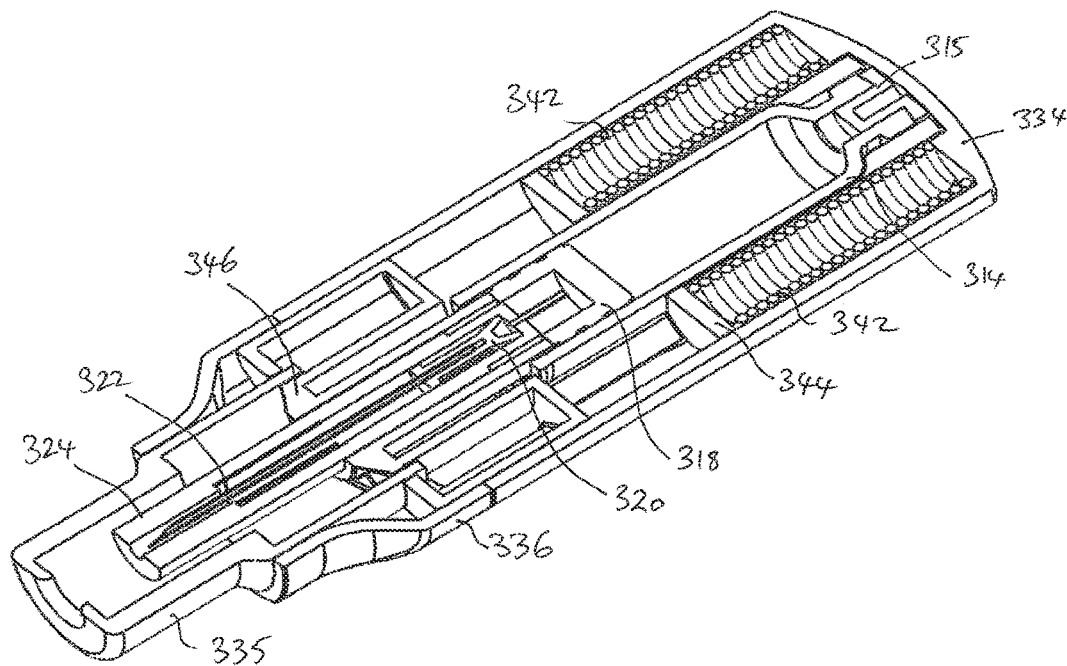
FIG. 34 is a perspective cross-section of FIG. 33.

FIG. 33 is a cross-section of a fourth embodiment of the invention, prior to use. In the fourth embodiment, the needle insertion mechanism is driven by the pressure of the drug. FIG. 34 is a perspective cross-section of FIG. 34.

The device shown in FIGS. 33 and 34 comprises a drug container 314 containing a drug 316. In this embodiment, the drug container is a glass vial, but it may be made from any suitable material. The drug container 314 may be filled from a front or a rear end and is sealed at the rear end with a stopper 315. A front outlet is sealed by plunger 318. Plunger 318 is formed from an elastomeric material and is fixed to chassis 346. A needle assembly is positioned forward of the drug container and comprises a hypodermic needle 322 held in needle hub 320. The needle hub is held within a generally tubular needle shuttle 324. The rear end of the needle hub 320 forms a cup seal with the interior of the shuttle 324.

Figure 35:
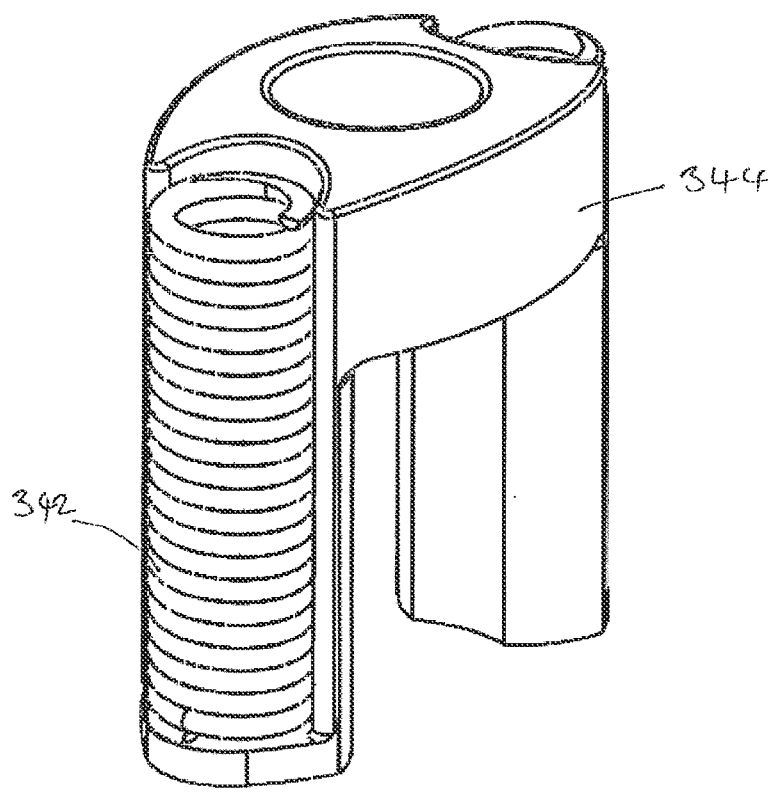
FIG. 35 is a perspective view of the pusher element and compression springs of FIG. 33.

A drive assembly, comprising a pair of compression springs 342 held between a rear housing 334 of the device and a pusher element 344, is positioned at the rear of the device. The drive assembly urges the pusher element 344 in a forward direction. The pusher element engages a rear of the drug container 314 and so urges the drug container in a forward direction. The pusher element and compression springs are shown in perspective view in FIG. 35. In the initial position as shown in FIG. 33, the drug container is held stationary by the drug and the plunger 318. Only when the drug is able to escape from the drug container can the drug container move forward.

A skin contact element 335 is provided at a front end of the device within a front housing 336. The front housing 336 is fixed to the chassis 346 and the rear housing 334. The skin contact element 335 is biased into a forward position by a biasing spring (not shown for clarity). The skin contact element 335 is initially held against the front housing to prevent expansion of the biasing spring.

Figure 36:
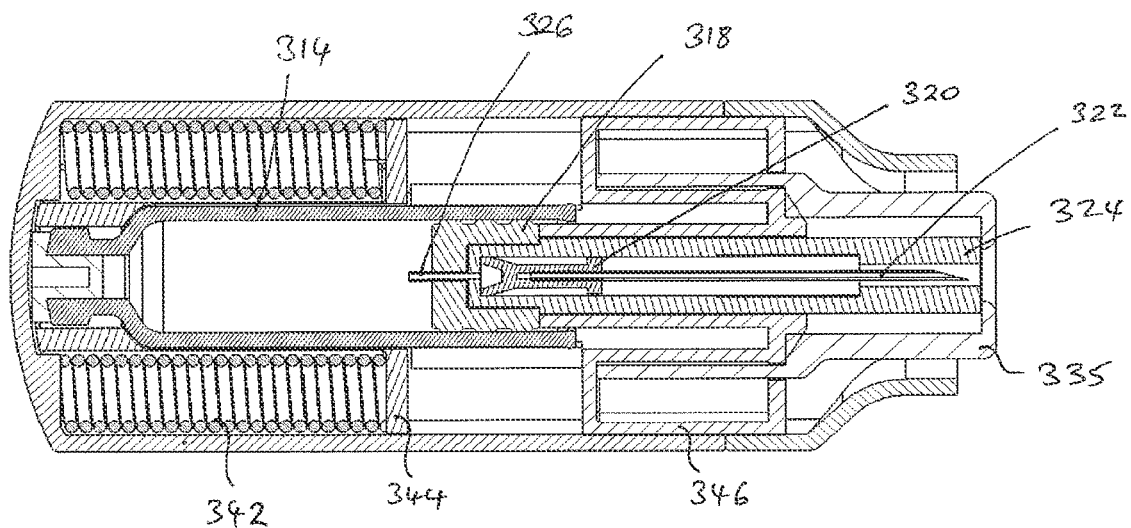
FIG. 36 shows the device of FIG. 33 with the skin contact element depressed.

In order to operate the device, the skin contact element 335 is pressed against an injection site against the action of the biasing spring. This moves the skin contact element rearward to contact the shuttle 324 and drive the shuttle rearward, as shown in FIG. 36. The shuttle has a hollow piercing element 326 formed on its rearward end. As the shuttle is driven back by the skin contact element, the piercing element pierces the plunger 318. The drug is now able to escape through the piercing element to contact the rear of the needle hub 320.

Figure 37:
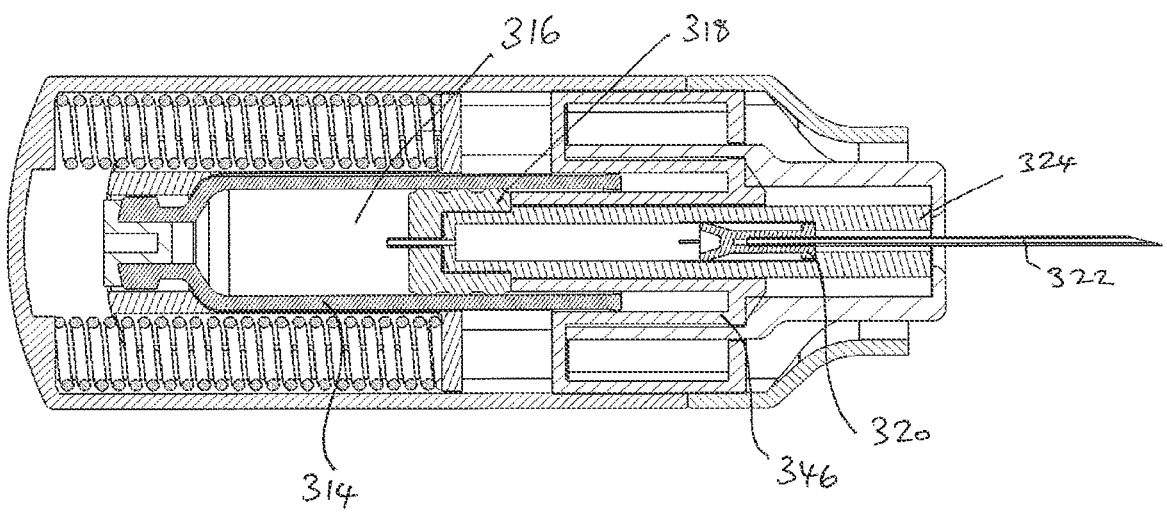
FIG. 37 shows the device of FIG. 36 with the needle moved to an insertion position.

The pressure of the drug on the needle hub drives the needle hub 320 and needle 322 forward through the shuttle 324. The seal formed by the needle hub with the interior of the shuttle, which is energised by the pressure of the drug, ensures that drug cannot escape past the needle. The needle is thereby driven to an insertion position, as shown in FIG. 37.

Figure 38:
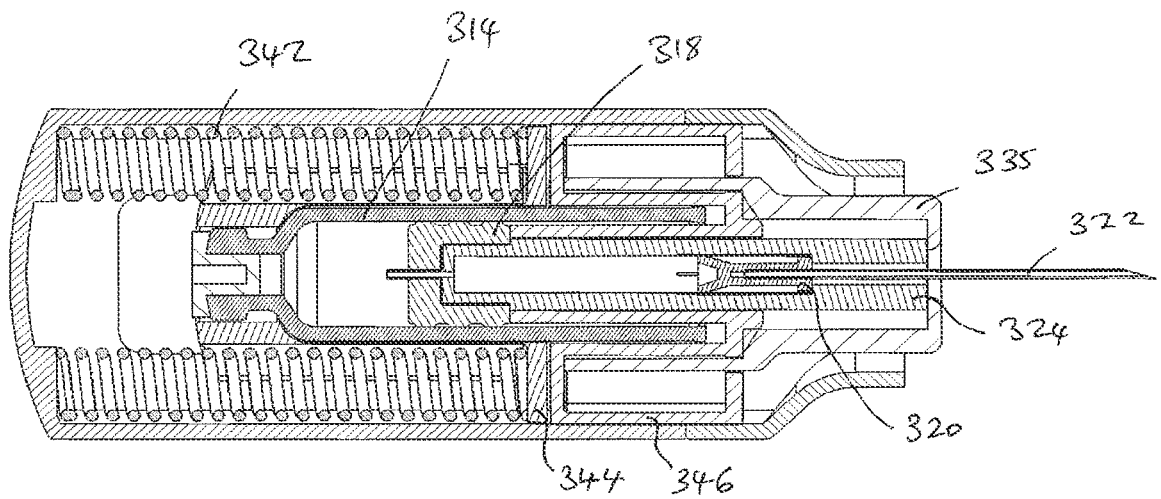
FIG. 38 shows the device of FIG. 37 after drug delivery has been completed.

The forward end of the interior of the shuttle has a section with a larger diameter than the rear end. This means that when the needle hub 320 reaches the insertion position, the drug 316 can pass between the interior of the shuttle 324 and the needle hub 320. The needle hub includes apertures that expose the rear end of the needle 322. As a result, the drug can pass into a rear end of the needle 322 and into the injection site. A front end of the needle hub 320 forms a seal with the front end of the shuttle 324 so that drug must escape solely through the needle. As the drug passes through the needle 322, the drug container is urged forward by the drive assembly to a stop position, as shown in FIG. 38. The stop position is defined by the point at which the pusher element 344 contacts the chassis 346. The impact of the pusher element 344 on the chassis 346 provides an audible indication of the completion of the drug delivery.

Figure 39:
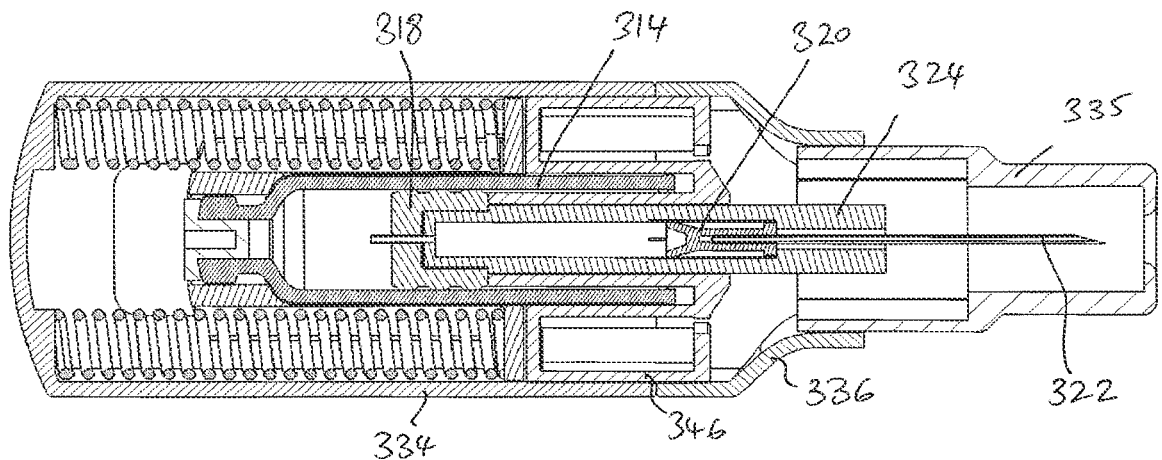
FIG. 39 shows the device of FIG. 38 with the skin contact element urged forward to cover the needle.

Following completion of the drug delivery, the device can be removed from the injection site. The skin contact element 335 can then move forward under the influence of the biasing spring to cover the needle 322, as shown in FIG. 39.

Figure 40:
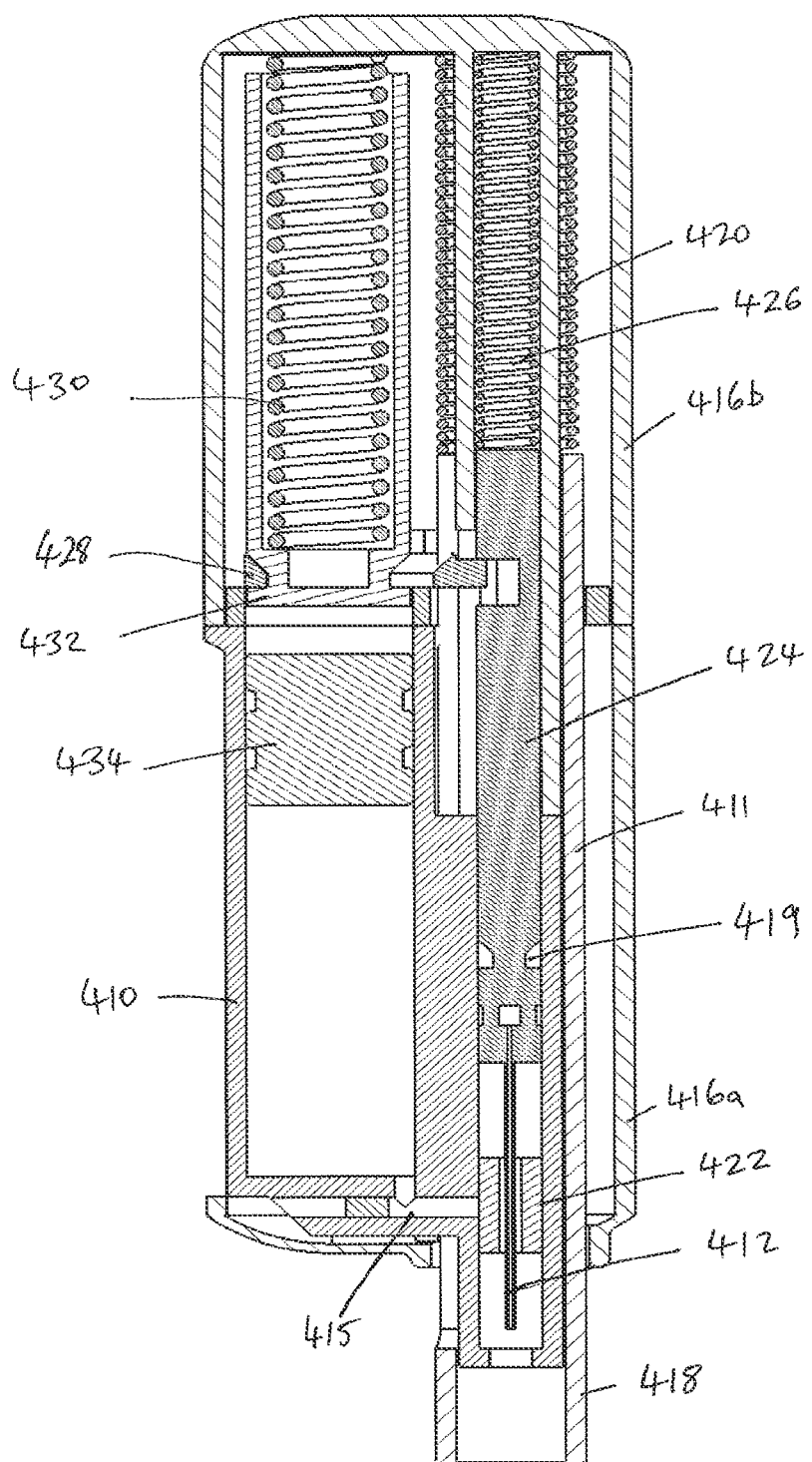
FIG. 40 is a cross section of a fifth embodiment of the invention.

FIG. 40 is a cross section of a fifth embodiment of the invention. In the fifth embodiment the needle and needle insertion mechanism are positioned adjacent the drug container and drug ejection mechanism, as in the third embodiment described above. However, the drug is not pressurised prior to needle insertion. Instead, the plunger is acted on by a piston only after the needle insertion has been completed.

The device shown in FIG. 40 comprises a front housing 416a and a rear housing 416b. The front housing 416a includes a drug containing portion 410 containing a drug. The front housing also includes a needle assembly holding portion 411. A needle assembly is within the needle containing portion 411 and includes a hypodermic needle 412 fixed to a needle hub 424. A first drive spring 426 is provided to move the needle forward through the housing and into a patient. A second drive spring 430 is provided to drive a piston 432 through the drug containing portion to push a plunger 434 and subsequently to eject the drug. The drug passes through a conduit 415 formed in the front housing to an opening in the needle hub and then through the needle into the patient, as will be described.

In the initial position, prior to use as shown in FIG. 40, a sealing element 422 is positioned around the needle 412 and seals the conduit 415 to ensure the drug remains in the drug containing portion. The plunger 434 seals the distal end of the drug containing portion.

Figure 41:
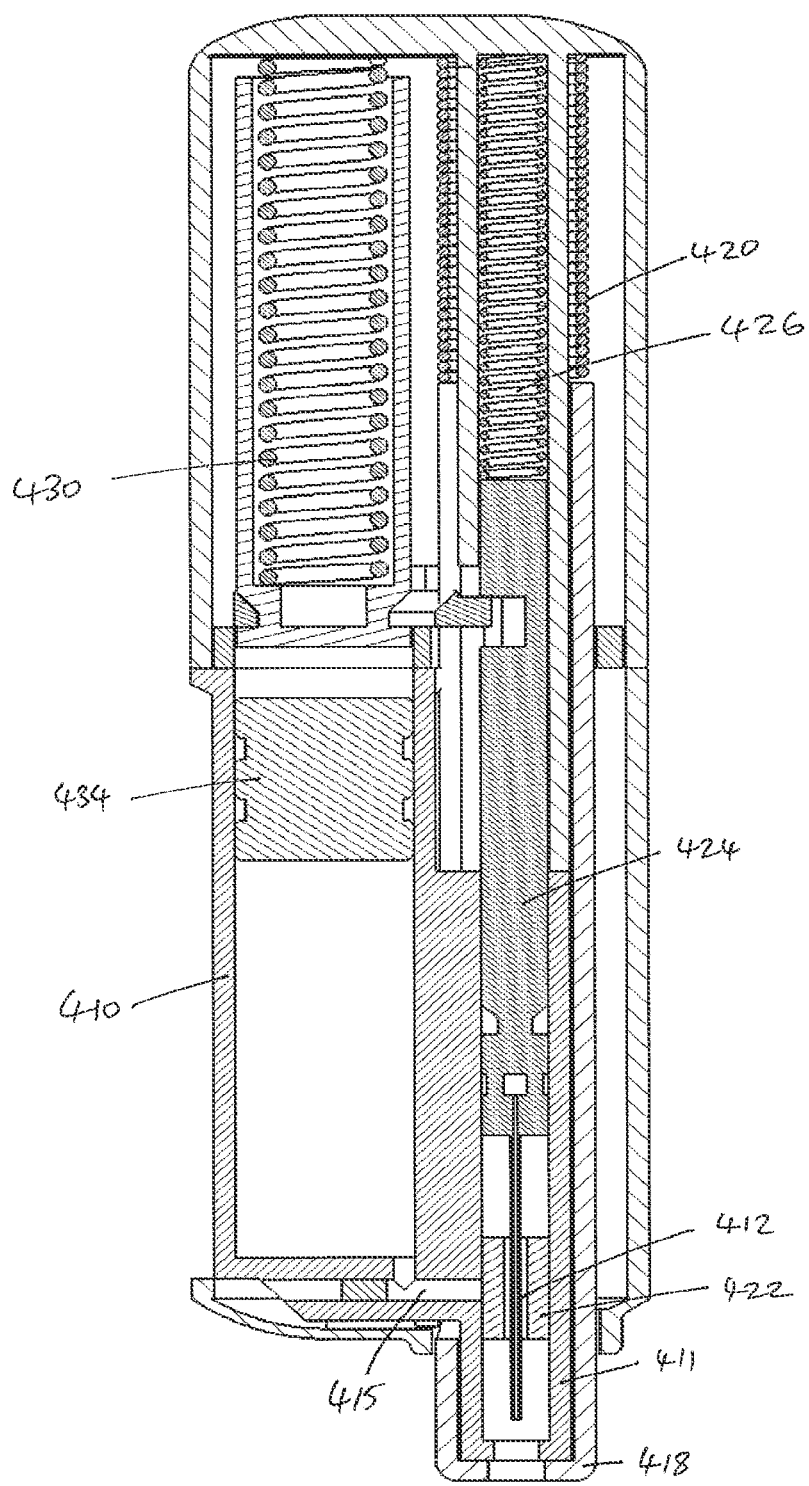
FIG. 41 shows the device of FIG. 40 with the skin contact element depressed.

The housing includes a skin contact element 418 that is biased into a proximal position by a biasing spring 420. Biasing spring is retained between the skin contact element and a portion of the rear housing 416b. In operation the skin contact element 418 is pressed against and injection site and is moved against the biasing spring 420 distally relative to the front housing 416a. The front housing 416a includes engaging fingers (not shown) that engage notches 419 in the needle hub 424 and so restrain the needle hub from forward movement under the influence of first drive spring 426. The engaging fingers are prevented from moving out of engagement with the notches in the needle hub by the skin contact element 418. However, the skin contact element 418 includes an aperture or cavity (not shown) positioned so that when the skin contact element is moved distally relative to the front housing the apertures align with the engaging fingers and allow the engaging fingers to move out of the notches in the needle hub. This position is shown in FIG. 41.

Figure 42:
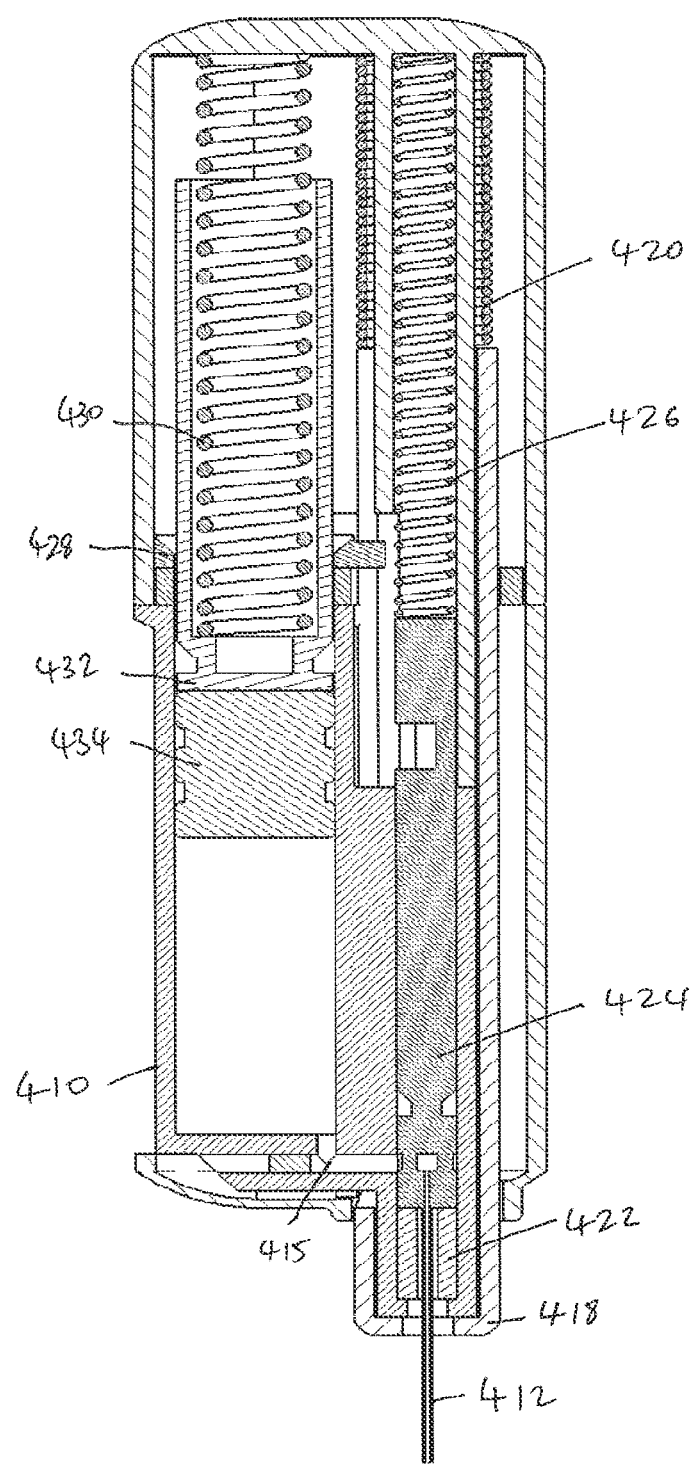
FIG. 42 shows the device of FIG. 41 with the needle 424 in an insertion position.

The needle hub is then free to move forward relative to the front housing 416a and the first drive spring. FIG. 42 shows the needle 422 in an insertion position. The needle hub 424 has been driven forward by the first drive spring 426 and has pushed the sealing element 422 forward with the front housing 416a. In an alternative embodiment, the sealing element 422 is fixed to the needle hub. In the position shown in FIG. 42, further forward movement of the needle hub is prevented by the front housing and the sealing element 422. In this position, an opening in the needle hub around the distal end of the needle is aligned with the conduit 415 so that the distal end of the needle is in fluid communication with the drug containing portion 410.

Movement of the needle hub 424 from the initial position to the insertion position releases the second drive spring 430, which is retained between the piston 432 and the rear housing 416b. In the initial position, the piston is restrained against proximal movement by locking member 428, which is also engaged with the needle hub. Movement of the needle hub out of the initial position allows the locking member 428 to be pushed out of engagement with the piston by the second drive spring. The piston is then free to move proximally through the drug containing portion.

Figure 43:
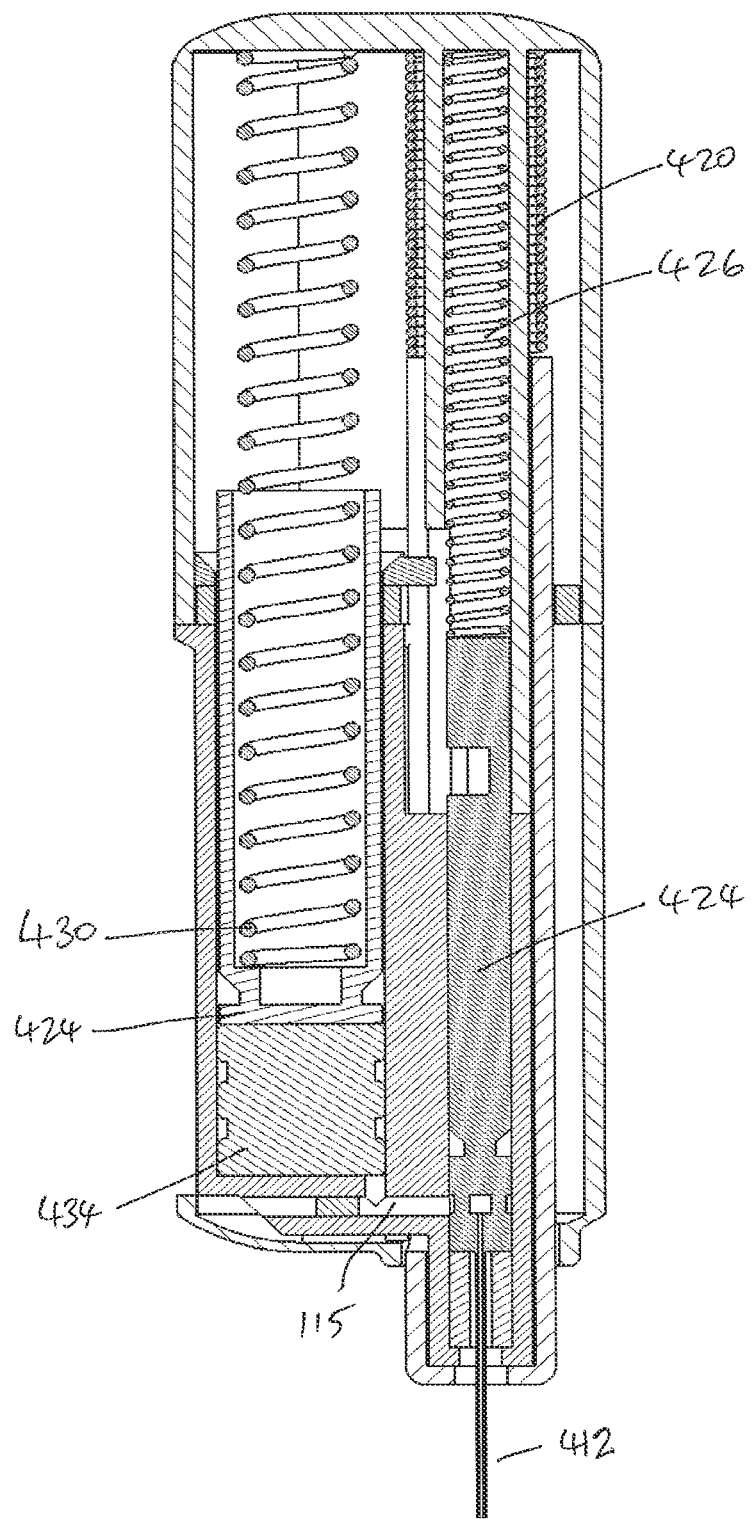
FIG. 43 shows the device of FIG. 42 after the piston has been moved through the drug containing portion by the second drive spring.

FIG. 43 shows the fifth embodiment after the piston 432 has been moved through the drug containing portion by the second drive spring 430. The drug has been pushed through conduit 115 and out through the needle 412 into the patient.

Figure 44:
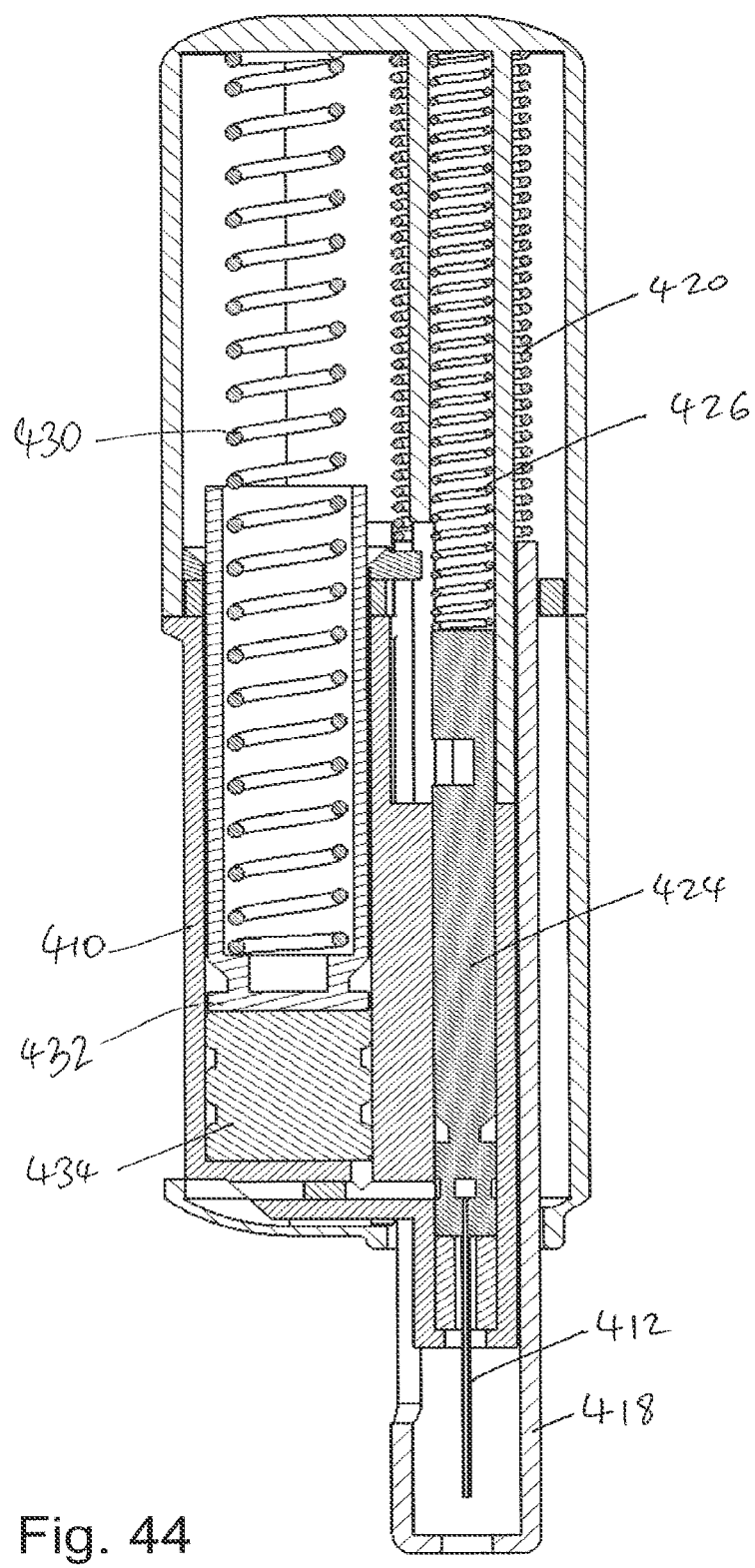
FIG. 44 shows the device of FIG. 43 after it has been removed from the injection site.

FIG. 44 shows the device after it has been removed from the injection site. The skin contact element 418 is moved to a proximal position covering the needle 412 owing to the action of the biasing spring 420. Engagement of a portion of the skin contact element 418 with the needle hub 424 prevents further proximal movement of the skin contact element 418. The skin contact element thereby provides a needle cover to prevent needle stick injuries following use of the device.

What is claimed is:

1. A drug delivery device comprising:
    a drug container assembly containing a drug, and a plunger positioned within the drug container assembly, the drug container assembly having an outlet for dispensing the drug, wherein, in an initial position, the outlet is sealed;
    a hypodermic needle through which the drug is delivered in use;
    a needle insertion mechanism operable to move the hypodermic needle relative to the drug container assembly and configured to insert the hypodermic needle automatically into the injection site;
    a drive mechanism comprising a first stored energy source operable to apply pressure on the plunger or the drug container assembly to pressurise the drug;
    a first release mechanism operable to unseal the outlet after the drug has been pressurised; and
    a second drug container assembly containing a second drug, the drug and the second drug being the same or different,
    wherein the device is configured such that, in use, the drug and the second drug are delivered through a single delivery conduit,
    wherein the device is configured such that hydraulic pressure of the drug, provided by the release of the first stored energy source, is used to move the needle insertion mechanism.

2. A drug delivery device according to claim 1, wherein an interior of the hypodermic needle is not in contact with the drug before operation of the first release mechanism.

3. A drug delivery device according to claim 1, wherein, in use, operation of the first release mechanism releases the needle insertion mechanism and unseals the outlet.

4. A drug delivery device according to claim 1, wherein the device is configured such that the first release mechanism is operable only when a front end of the device, through which the drug is delivered, is pressed against an injection site.

5. A drug delivery device according to claim 1, further comprising a main housing and a skin contact element, the skin contact element forming a front end of the device, movement of the skin contact element relative to the main housing from the initial position to an insertion position operating or allowing the operation of the first release mechanism.

6. A drug delivery device according to claim 5, wherein the first release mechanism comprises a first locking surface on the skin contact element that in the initial position limits relative movement between a needle hub and the main housing or the drug container assembly.

7. A drug delivery device according to claim 6, further comprising a biasing element between the skin contact element and the main housing or the drug container assembly, the biasing element urging the skin contact element in a proximal direction.

8. A drug delivery device according to claim 1, wherein the hypodermic needle is provided in a needle hub that extends into the drug container assembly and, in the initial position, seals the outlet.

9. A drug delivery device according to claim 8, wherein, in the initial position, the needle hub is restrained from proximal movement by a locking element, and wherein the first release mechanism is operable to release the needle hub from the locking element to allow the needle hub to be driven in a proximal direction by the pressure of the drug.

10. A drug delivery device according to claim 9, wherein the needle hub is configured such that movement of the needle hub in the proximal direction from the initial position to an insertion position unseals the outlet.

11. A drug delivery device according to claim 1, wherein:
    the drug container assembly comprises a separation seal that seals the drug in the drug container assembly from a third drug in the drug container assembly or from the second drug in the second drug container assembly and operation of the first release mechanism automatically unseals the separation seal,
    and/or
    the second drug container assembly comprises a second separation seal that seals the second drug in the second drug container assembly from a fourth drug in the second drug container assembly or from the drug in the drug container assembly and operation of the first release mechanism automatically unseals the second separation seal.

12. A drug delivery device according to claim 1, wherein the drug container assembly and the second drug container assembly are not axially aligned.

13. A drug delivery device according to claim 1, wherein the drug container assembly is configured to provide the drug to the hypodermic needle and the second drug container assembly is configured to provide the second drug to the hypodermic needle.

14. A drug delivery device according to claim 13, wherein the drug container assembly and the second drug container assembly are configured to provide the drug and the second drug to the hypodermic needle simultaneously.

15. A drug delivery device according to claim 1, wherein, in the initial position, the outlet of the drug container assembly and an outlet of the second drug container assembly are sealed by a sealing element surrounding the hypodermic needle.

16. A drug delivery device according to claim 1, wherein the device comprises a first compression spring configured to expel the drug from the drug container assembly and a second compression spring, different to the first compression spring, configured to expel the second drug from the second container assembly.

17. A drug delivery device comprising:
    a drug container assembly containing a drug, and a plunger positioned within the drug container assembly, the drug container assembly having an outlet for dispensing the drug, wherein, in an initial position, the outlet is sealed;
    a hypodermic needle through which the drug is delivered in use;

a drive mechanism comprising a first stored energy source operable to apply pressure on the plunger or the drug container assembly to pressurise the drug;

a first release mechanism operable to unseal the outlet after the drug has been pressurised; and a second drug container assembly containing a second drug, the drug and the second drug being the same or different, wherein the device is configured such that, in use, the drug and the second drug are delivered through a single delivery conduit, wherein the hypodermic needle is provided in a needle hub that extends into the drug container assembly and, in the initial position, seals the outlet.

18. A drug delivery device according to claim 17, wherein an interior of the hypodermic needle is not in contact with the drug before operation of the first release mechanism.

19. A drug delivery device according to claim 17, wherein the device is configured such that the first release mechanism is operable only when a front end of the device, through which the drug is delivered, is pressed against an injection site.

20. A drug delivery device according to claim 17, wherein, in the initial position, the needle hub is restrained from proximal movement by a locking element, and wherein the first release mechanism is operable to release the needle hub from the locking element to allow the needle hub to be driven in a proximal direction by the pressure of the drug.

* * * * *